(12) United States Patent
Bai

(10) Patent No.: US 12,195,433 B2
(45) Date of Patent: Jan. 14, 2025

(54) ORGANIC COMPOUND, PREPARATION METHOD THEREOF, AND DISPLAY PANEL

(71) Applicant: WUHAN CHINA STAR OPTOELECTRONICS SEMICONDUCTOR DISPLAY TECHNOLOGY CO., LTD., Wuhan (CN)

(72) Inventor: Keyan Bai, Wuhan (CN)

(73) Assignee: WUHAN CHINA STAR OPTOELECTRONICS SEMICONDUCTOR DISPLAY TECHNOLOGY CO., LTD., Wuhan (CN)

(*) Notice: Subject to any disclaimer, the term of this patent is extended or adjusted under 35 U.S.C. 154(b) by 832 days.

(21) Appl. No.: 17/419,690

(22) PCT Filed: May 24, 2021

(86) PCT No.: PCT/CN2021/095380
§ 371 (c)(1),
(2) Date: Jun. 29, 2021

(87) PCT Pub. No.: WO2022/205587
PCT Pub. Date: Oct. 6, 2022

(65) Prior Publication Data
US 2023/0174494 A1    Jun. 8, 2023

(30) Foreign Application Priority Data
Mar. 29, 2021   (CN) .......................... 202110334523.X

(51) Int. Cl.
| | |
|---|---|
| C07D 241/46 | (2006.01) |
| C07D 403/10 | (2006.01) |
| C07D 413/10 | (2006.01) |
| C07F 7/08 | (2006.01) |
| H10K 50/11 | (2023.01) |
| H10K 85/40 | (2023.01) |
| H10K 85/60 | (2023.01) |

(52) U.S. Cl.
CPC ......... *C07D 241/46* (2013.01); *C07D 403/10* (2013.01); *C07D 413/10* (2013.01); *C07F 7/0812* (2013.01); *H10K 50/11* (2023.02); *H10K 85/40* (2023.02); *H10K 85/615* (2023.02); *H10K 85/657* (2023.02); *H10K 85/6572* (2023.02)

(58) Field of Classification Search
CPC .................................................... C07D 241/46
See application file for complete search history.

(56) References Cited

U.S. PATENT DOCUMENTS

2014/0042412 A1   2/2014  Ryu et al.
2016/0308144 A1*  10/2016  Lee ..................... H10K 85/626

FOREIGN PATENT DOCUMENTS

| CN | 108203417 A | 6/2018 | |
|---|---|---|---|
| CN | 109761822 A | 5/2019 | |
| CN | 110299460 A | 10/2019 | |
| CN | 110407817 A | 11/2019 | |
| CN | 110885317 A | 3/2020 | |
| CN | 111056959 A | 4/2020 | |
| CN | 111205272 A | 5/2020 | |
| CN | 111635391 A | 9/2020 | |
| CN | 112375002 A | 2/2021 | |
| JP | 2014037353 A | 2/2014 | |
| WO | WO-2010050781 A1 * | 5/2010 | ........... C07D 215/06 |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS RegistrySM) Sep. 2016 2 pages.*

* cited by examiner

*Primary Examiner* — Nizal S Chandrakumar
(74) *Attorney, Agent, or Firm* — PV IP PC; Wei Te Chung

(57) ABSTRACT

Embodiments of the present invention disclose an organic compound, a preparation method thereof, and a display panel. The organic compound is represented by the following general formula:

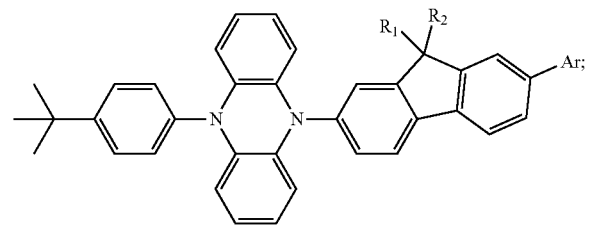

wherein Ar comprises any one or a combination of hydrogen, an isotope of hydrogen, an aromatic group, an arylamine group, a heteroarylamine group, and a fused ring group; and R1 and R2 are each independently any one or a combination of alkyl, alkoxy, heteroalkyl, and an aromatic group. In the embodiments of the present invention, by adding other electron-donating groups on the basis of a phenazine-fused fluorene structure, organic compounds with high mobility are obtained.

11 Claims, 1 Drawing Sheet

ORGANIC COMPOUND, PREPARATION METHOD THEREOF, AND DISPLAY PANEL

RELATED APPLICATIONS

This application is a Notional Phase of PCT Patent Application No. PCT/CN2021/095380 having international filing date of May 24, 2021, which claims the benefit of priority of Chinese Patent Application No. 202110334523.X filed on Mar. 29, 2021. The contents of the above applications are all incorporated by reference as if fully set forth herein in their entirety.

BACKGROUND OF INVENTION

Field of Invention

The present application relates to the field of display, and in particular to an organic compound, a preparation method thereof, and a display panel.

Description of Prior Art

In recent years, organic light-emitting diode (OLED) display panels have become more and more popular in the market.

At present, in the OLED display panels, energy levels and mobility of materials of light-emitting device layers have always been in contradictory relationships, and it is urgent to develop materials for the light-emitting device layers with matching energy levels and high mobility.

Therefore, there is an urgent need to provide an organic compound, a preparation method thereof, and a display panel to solve the above technical problems.

SUMMARY OF INVENTION

Embodiments of the present application provide an organic compound and a preparation method thereof, and a display panel, to alleviate the technical problem of low mobility of materials for light-emitting device layers.

In order to solve the above problems, the technical solutions provided by the present application are as follows:

Embodiments of the present application provide An organic compound, wherein the organic compound is represented by the following general formula:

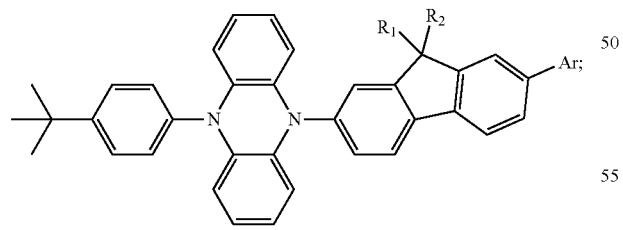

wherein Ar1 comprises any one or a combination of hydrogen, an isotope of hydrogen, an aromatic group, an arylamine group, a heteroarylamine group, and a fused ring group; and R1 and R2 are each independently any one or a combination of alkyl, alkoxy, heteroalkyl, and an aromatic group.

In one embodiment, Ar comprises any one or a combination of protium, deuterium, tritium, an aromatic group having 6 to 60 carbon atoms, an arylamine group having 6 to 60 carbon atoms, a heteroarylamine group having 6 to 60 carbon atoms, and a fused ring group having 10 to 60 carbon atoms; and R1 or R2 is any one or a combination of an alkyl group having 1 to 22 carbon atoms, an alkoxy group having 1 to 22 carbon atoms, a heteroalkyl group having 1 to 22 carbon atoms, and an aromatic group having 6 to 60 carbon atoms.

In one embodiment, Ar is an axisymmetric group containing a benzene ring.

In one embodiment, Ar is any one or a combination of the following groups:

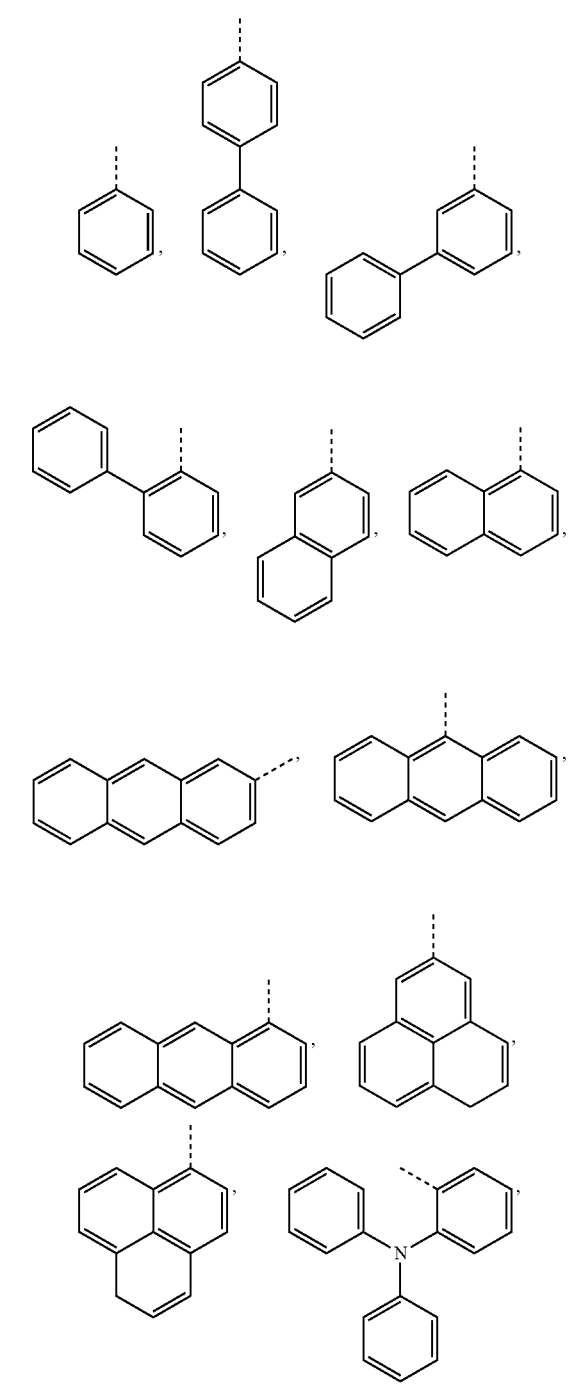

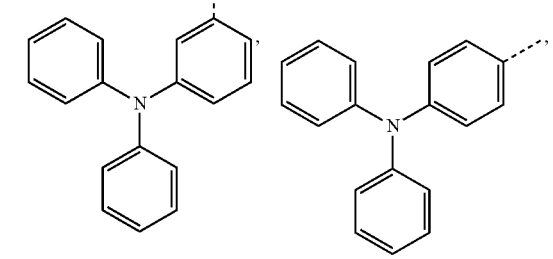
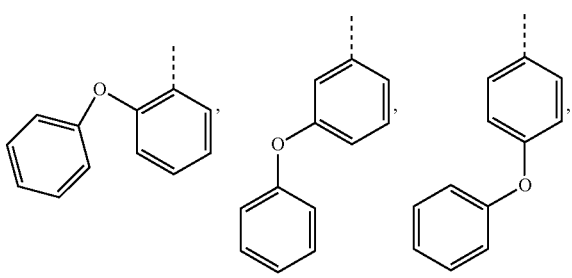
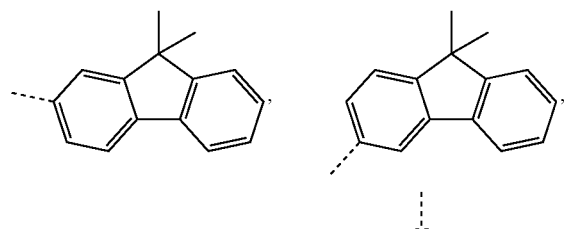
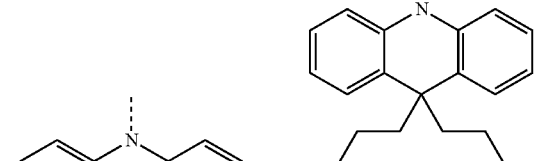
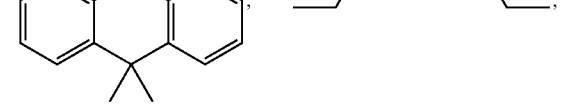
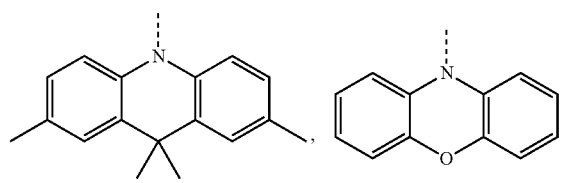
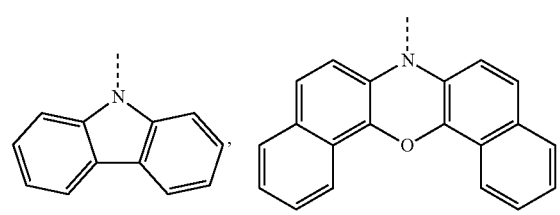
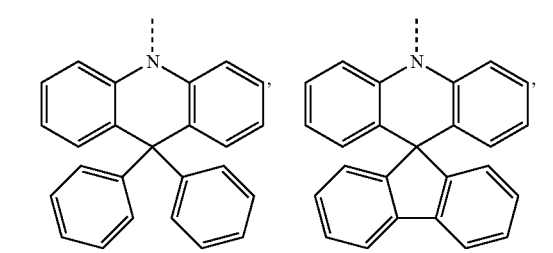
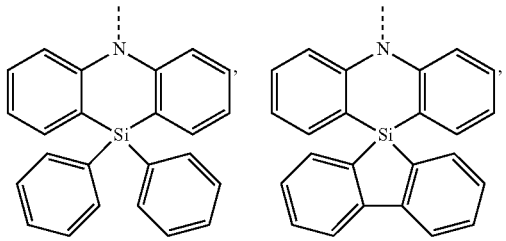
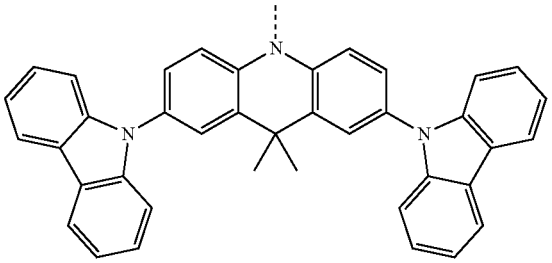
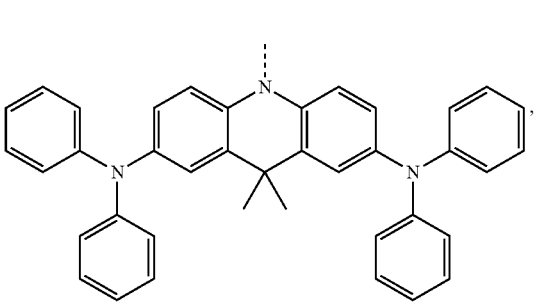
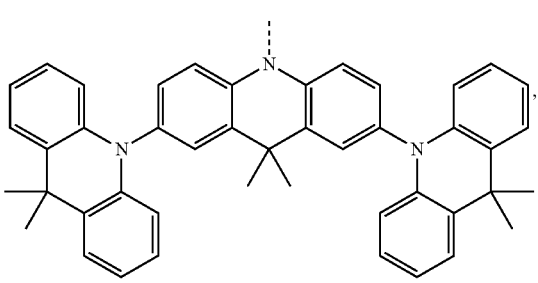
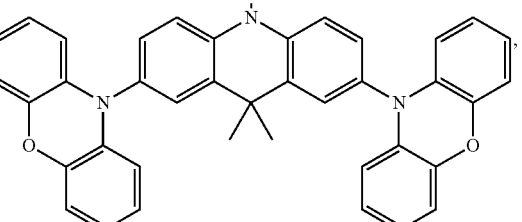
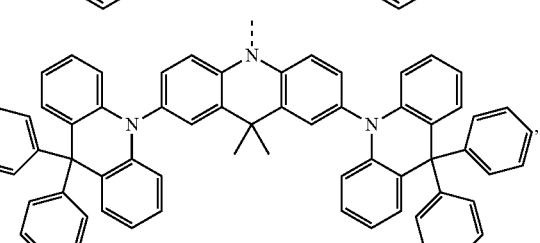

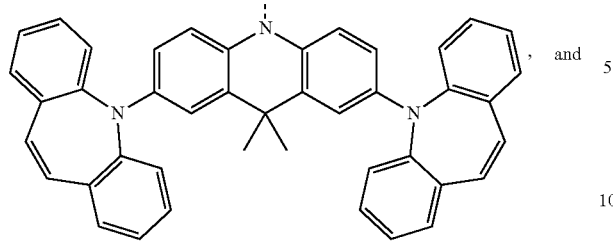

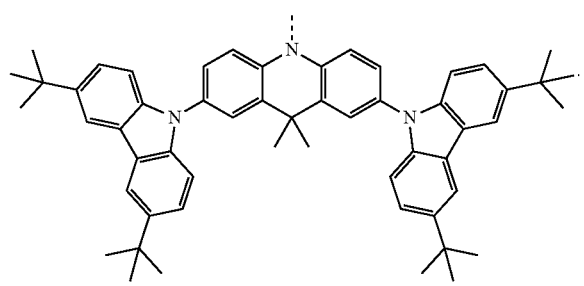

In one embodiment, the aromatic group comprises an oxygen-containing aromatic group or a silicon-containing aromatic group, the arylamine group comprises an oxygen-containing arylamine group or a silicon-containing arylamine group, and the fused ring group comprises any one of naphthalene, anthracene, and pyrene.

In one embodiment, Ar is any one or a combination of the following groups:

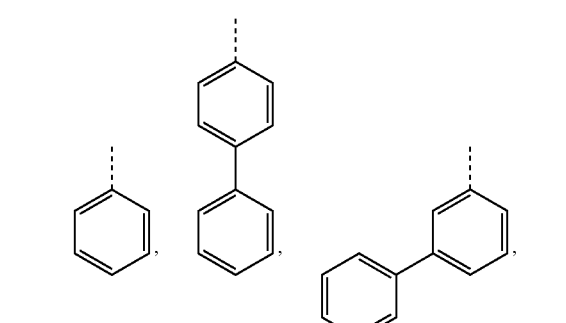

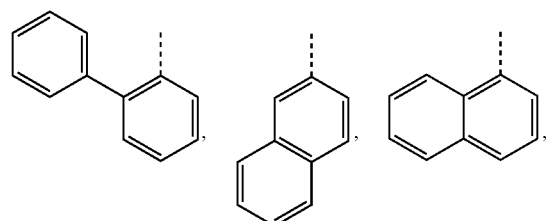

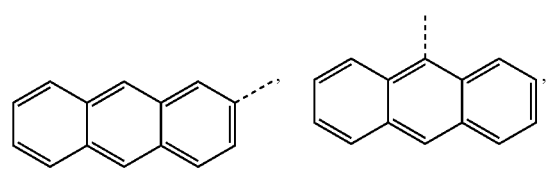

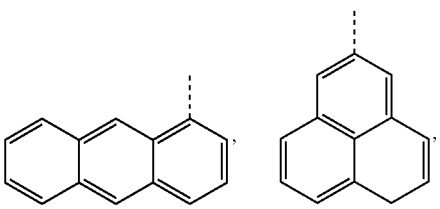

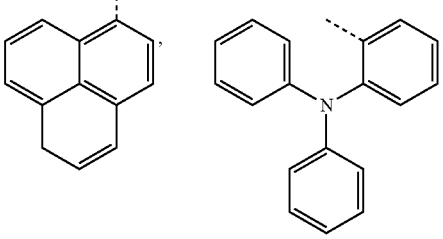

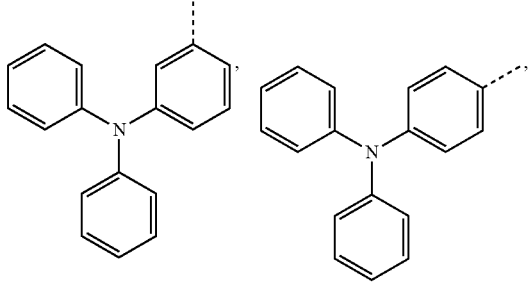

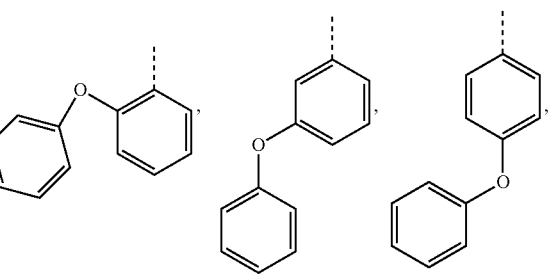

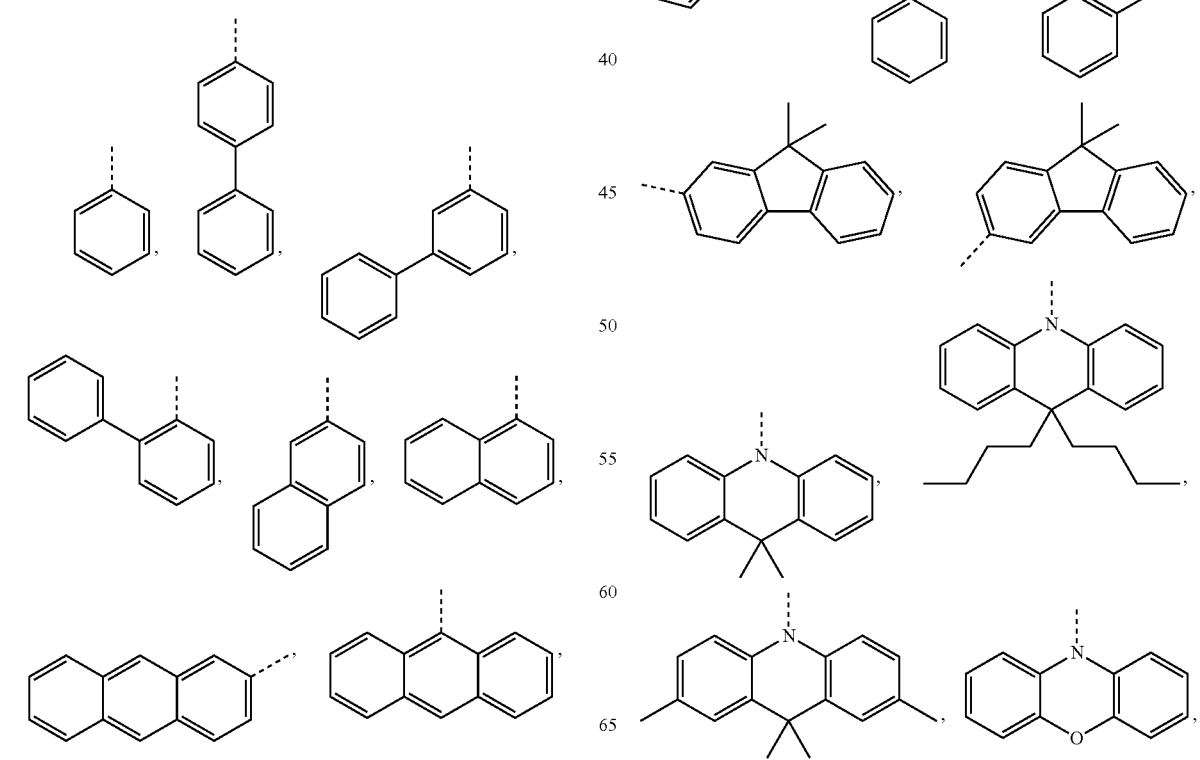

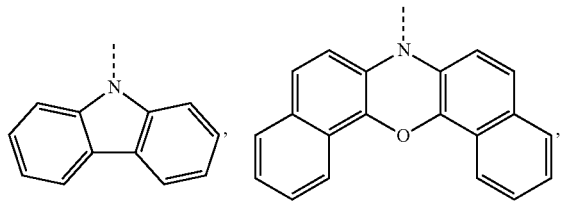
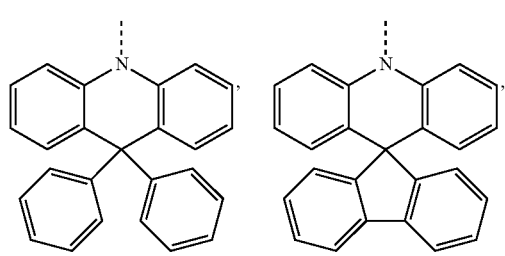
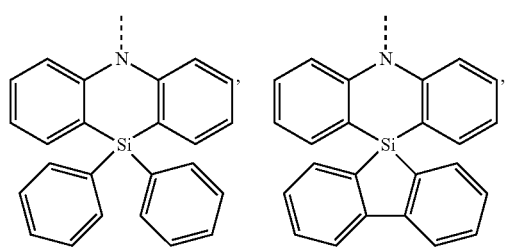
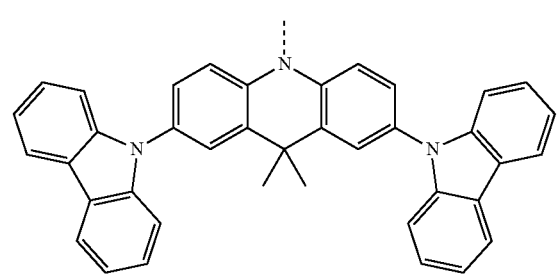
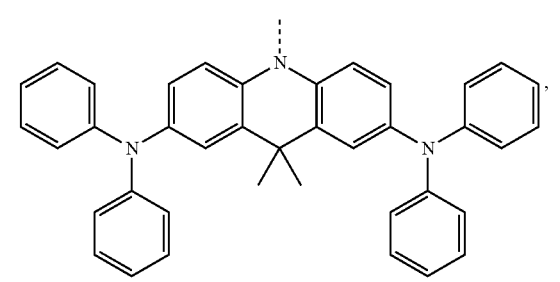
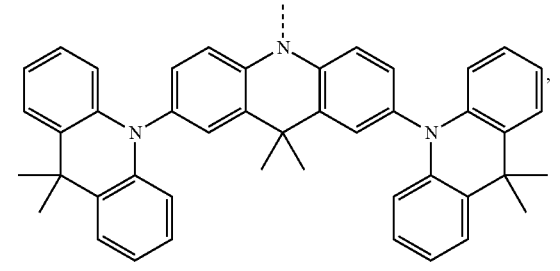
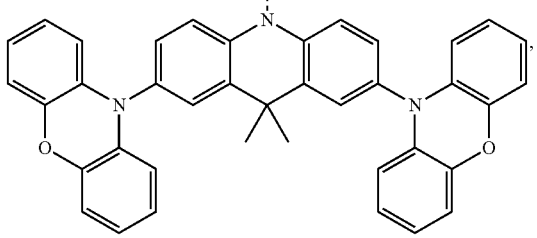
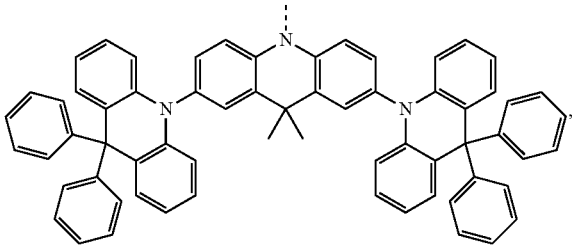
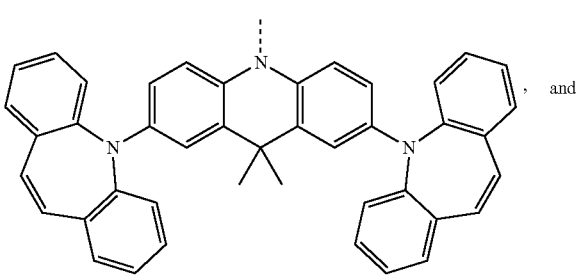
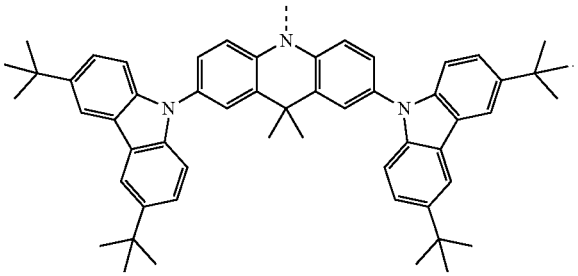
In one embodiment, R1 and R2 are each independently any one of methyl, ethyl, and phenyl.
In one embodiment, a structural formula of the organic compound is:
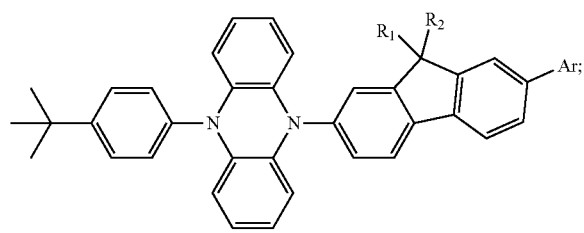
wherein Ar is an aromatic group having 6 to 60 carbon atoms or a heteroaromatic group having 6 to 60 carbon atoms.

In one embodiment, a structure of the organic compound comprises any one or a combination of the following:
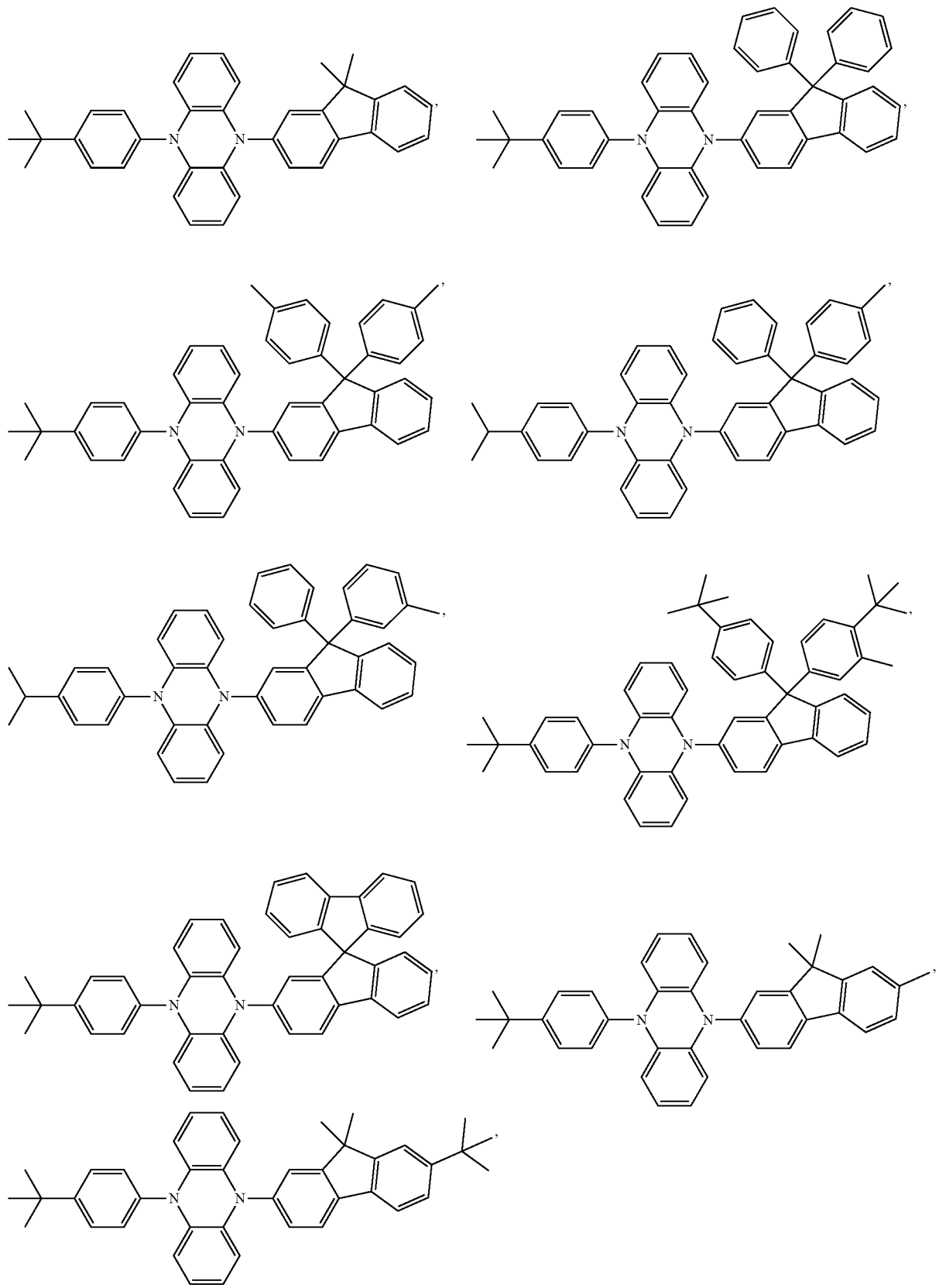

-continued
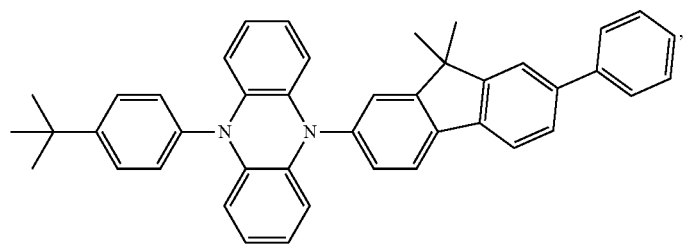
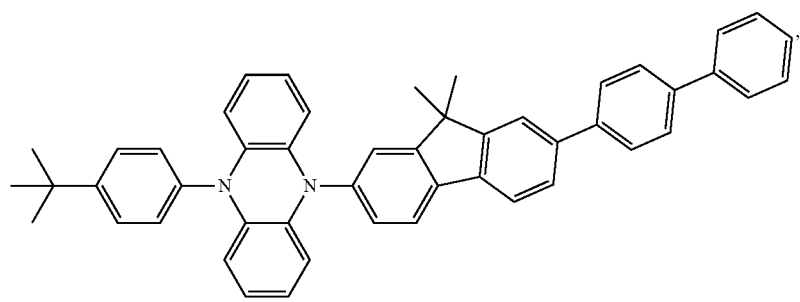
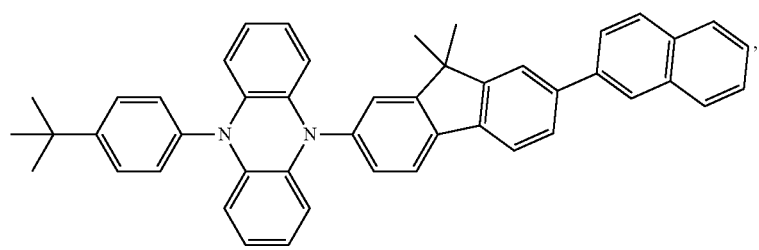
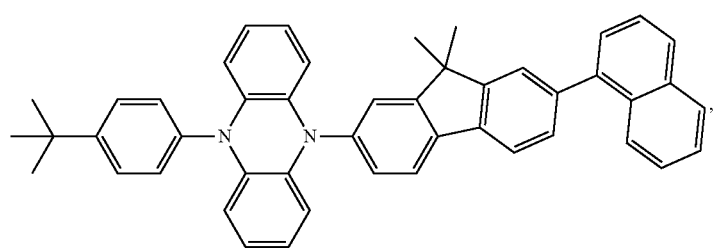
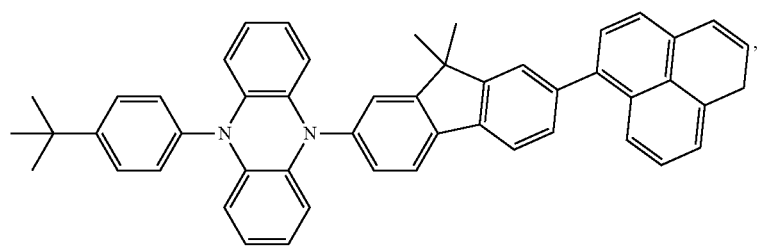
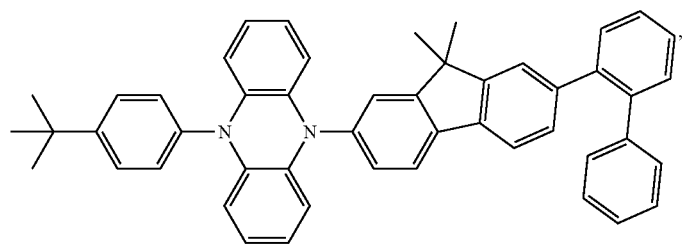

-continued
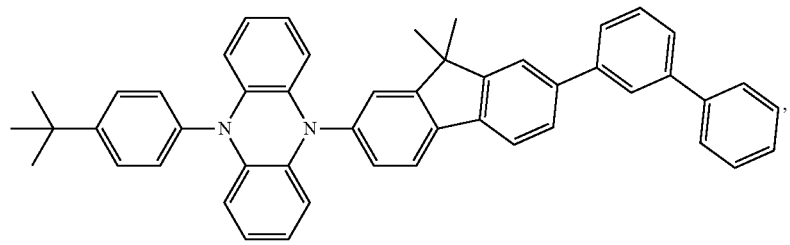
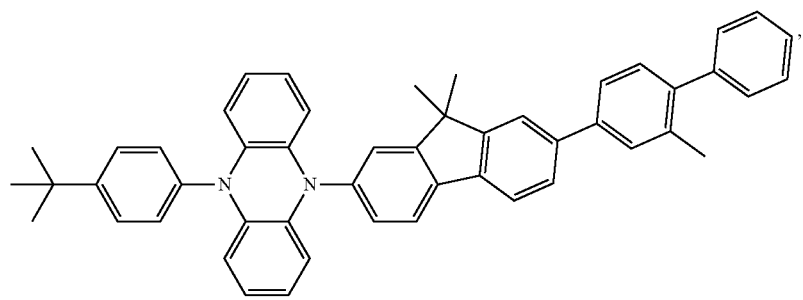
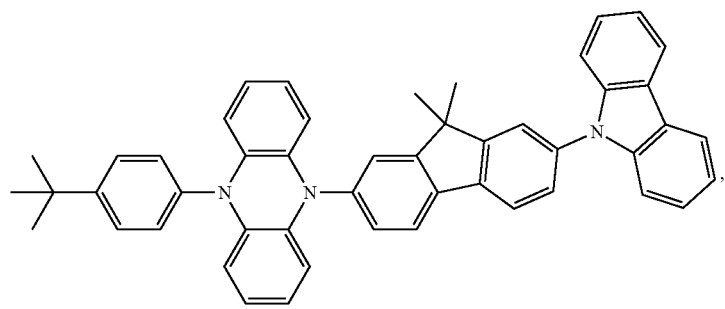
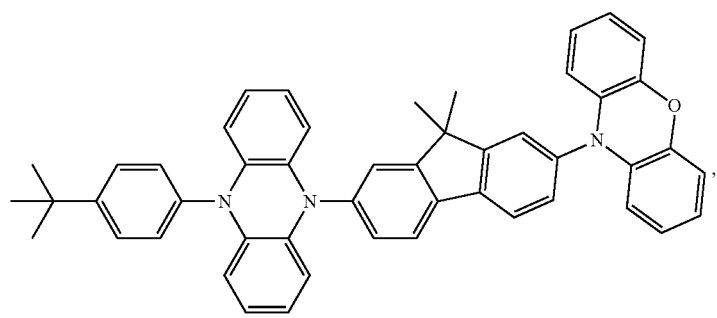
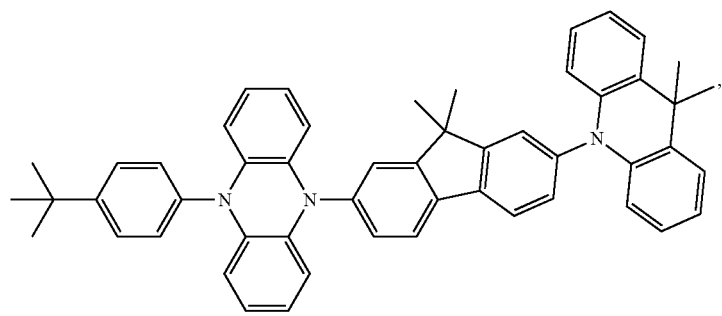

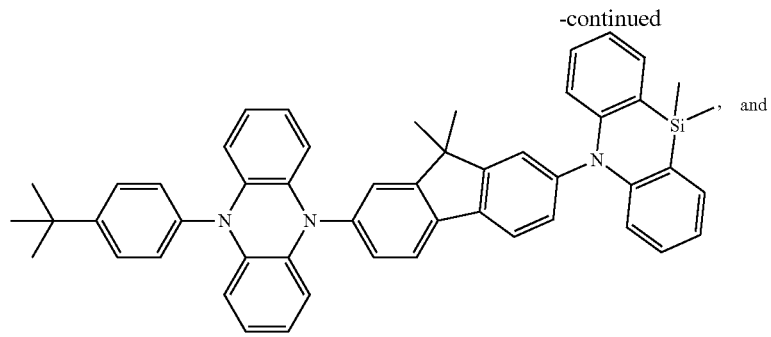, and

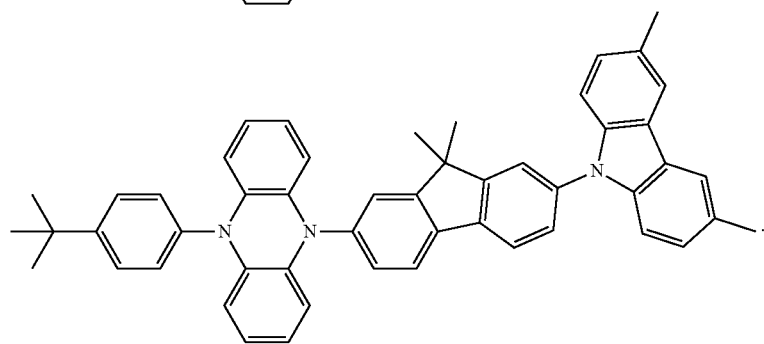

Another embodiment of the present application further provides a method of preparing an organic compound, which comprises:

mixing a first material and a second material to form the organic compound, and the organic compound is represented by the general formula (1):

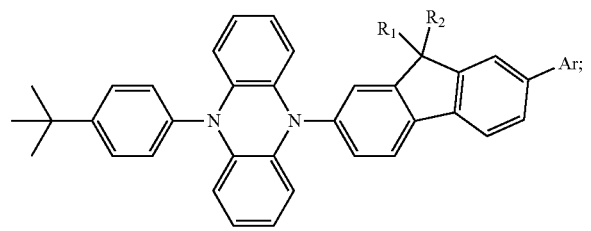

the first material is represented by the general formula (2):

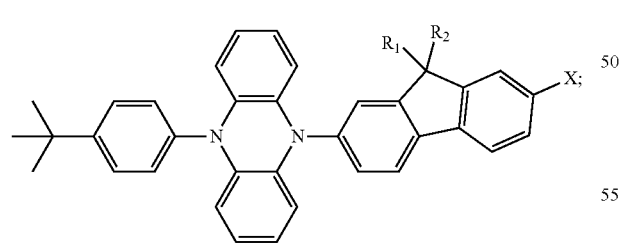

wherein R1 and R2 are each independently any one or a combination of alkyl, alkoxy, heteroalkyl, and an aromatic group; X is a halogen, and the second material comprises any one or a combination of an aromatic group, an arylamine group, a heteroarylamine group, and a fused ring group; and Ar comprises any one or a combination of hydrogen, an isotope of hydrogen, an aromatic group, an arylamine group, and a heteroarylamine group.

In one embodiment, a molar ratio of the first material to the second material is 1:1 to 1:3.

Yet another embodiment of the present application provides a display panel, comprising a light-emitting device layer, wherein the light-emitting device layer comprises an organic compound, and the organic compound is represented by the following general formula:

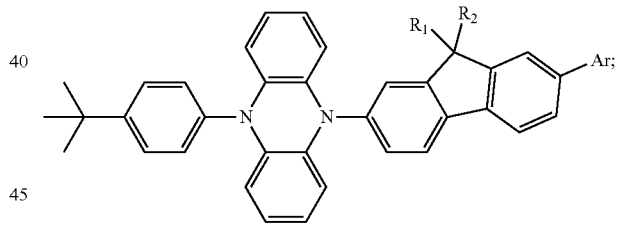

wherein Ar comprises any one or a combination of hydrogen, an isotope of hydrogen, an aromatic group, an arylamine group, a heteroarylamine group, and a fused ring group; and R1 and R2 are each independently any one or a combination of alkyl, alkoxy, heteroalkyl, and an aromatic group.

In one embodiment, Ar comprises any one or a combination of protium, deuterium, tritium, an aromatic group having 6 to 60 carbon atoms, an arylamine group having 6 to 60 carbon atoms, a heteroarylamine group having 6 to 60 carbon atoms, and a fused ring group having 10 to 60 carbon atoms; and R1 or R2 is any one or a combination of an alkyl group having 1 to 22 carbon atoms, an alkoxy group having 1 to 22 carbon atoms, a heteroalkyl group having 1 to 22 carbon atoms, and an aromatic group having 6 to 60 carbon atoms.

In one embodiment, Ar is an axisymmetric group containing a benzene ring.

In one embodiment, Ar is any one or a combination of the following groups:
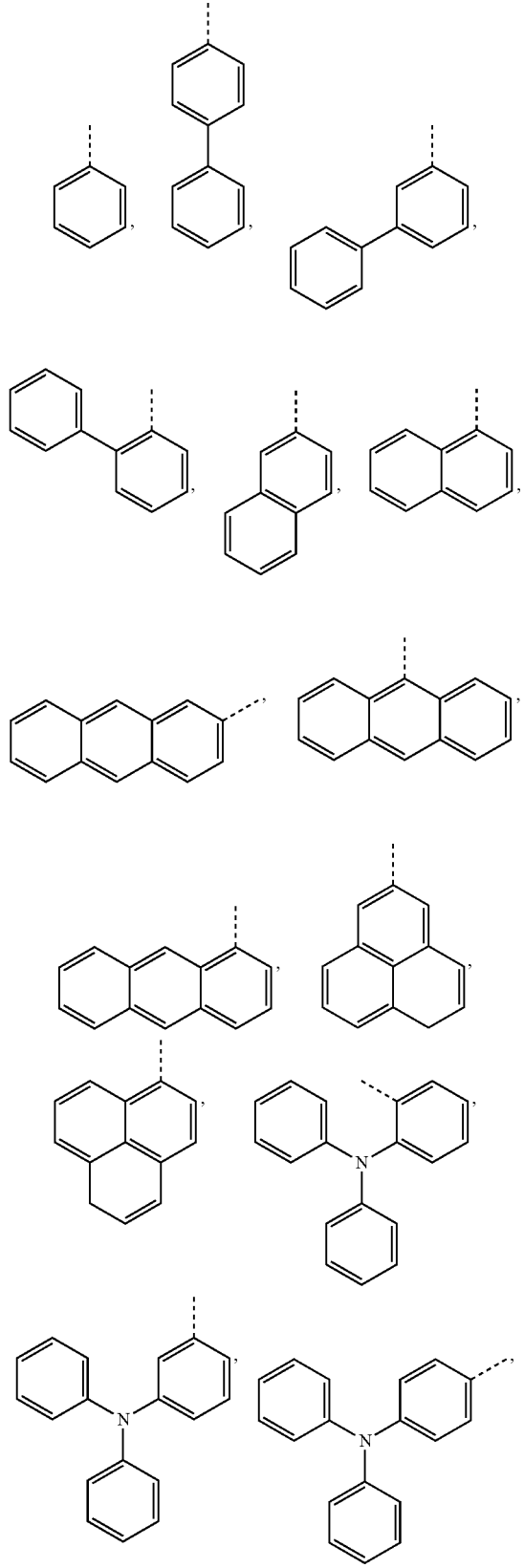
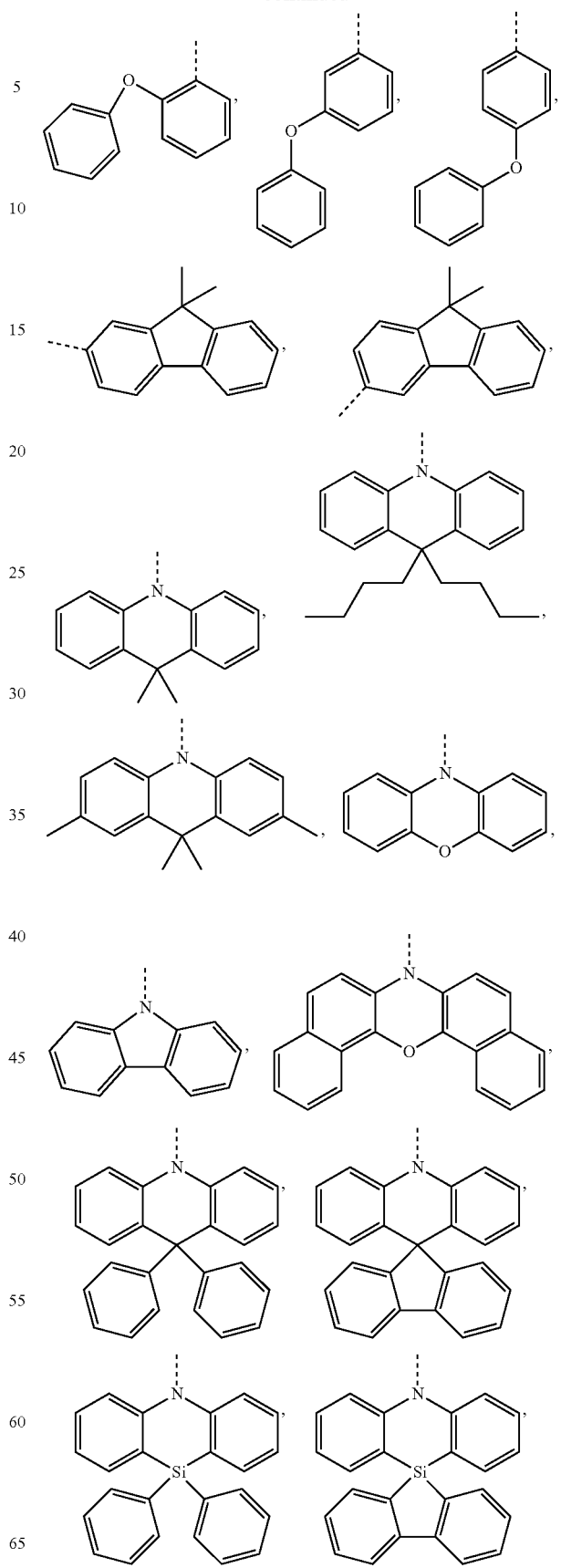

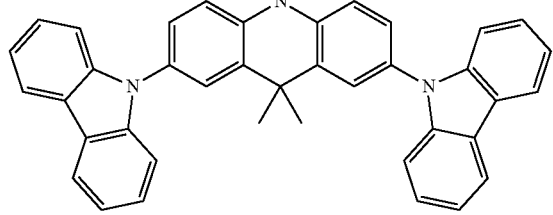

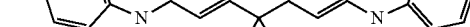

In one embodiment, the aromatic group comprises an oxygen-containing aromatic group or a silicon-containing aromatic group, the arylamine group comprises an oxygen-containing arylamine group or a silicon-containing arylamine group, and the fused ring group comprises any one of naphthalene, anthracene, and pyrene.

In one embodiment, Ar is any one or a combination of the following groups:

-continued
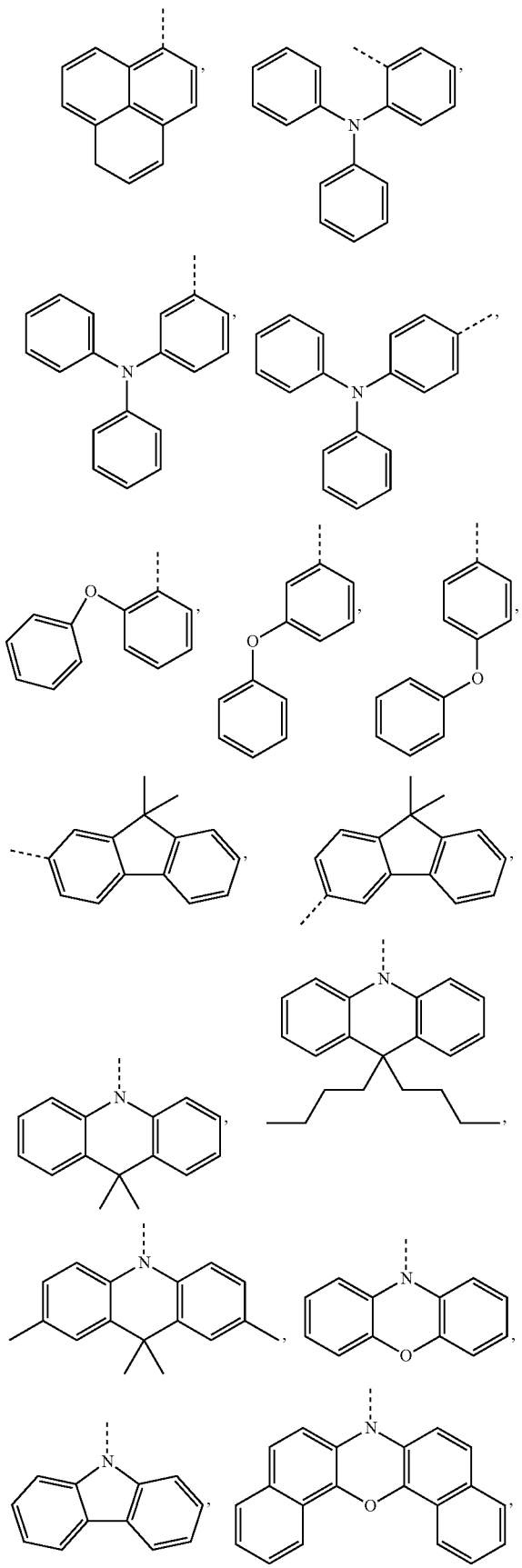
-continued
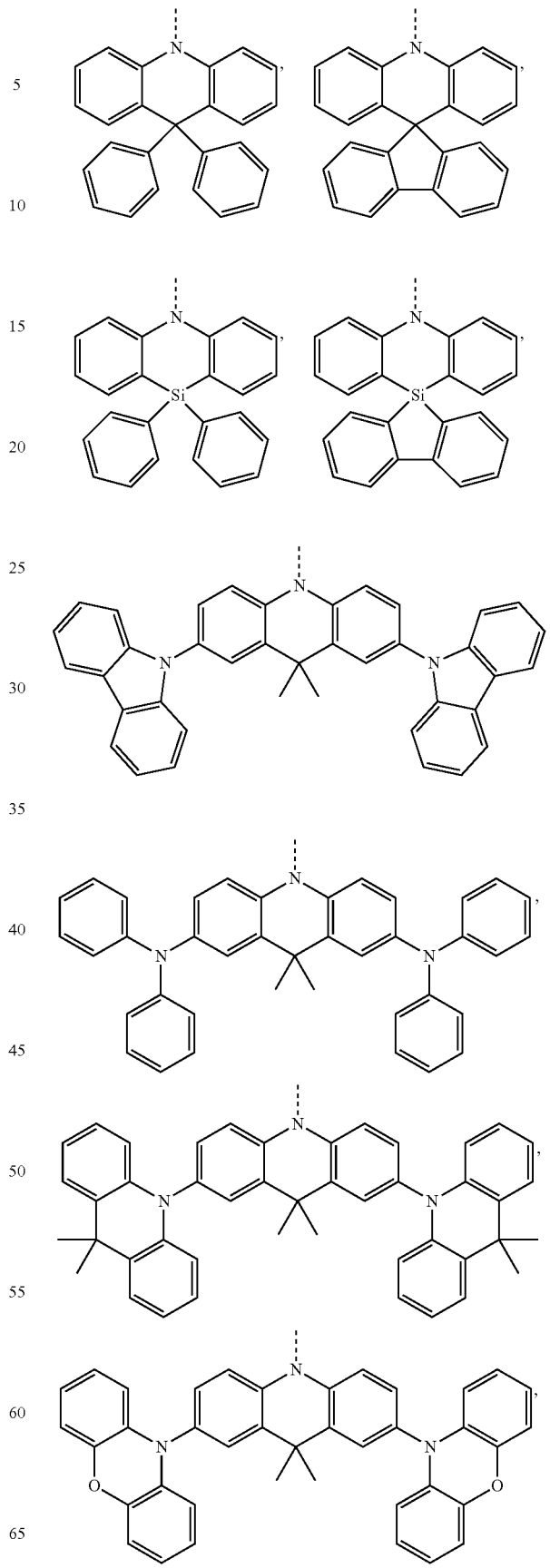

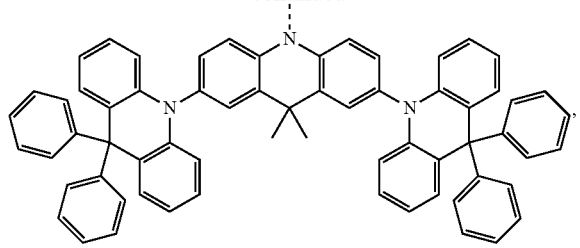,

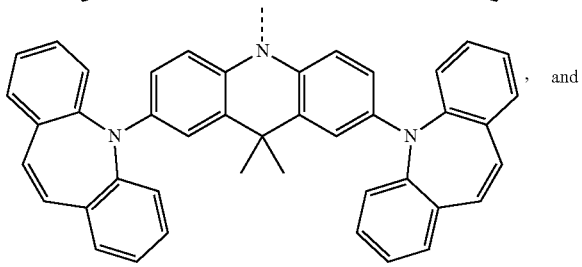, and

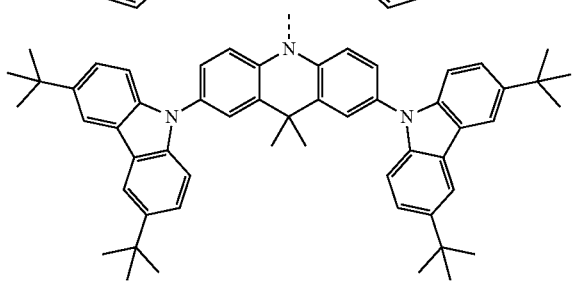

In one embodiment, R1 and R2 are each independently any one of methyl, ethyl, and phenyl.

In one embodiment, a structural formula of the organic compound is:

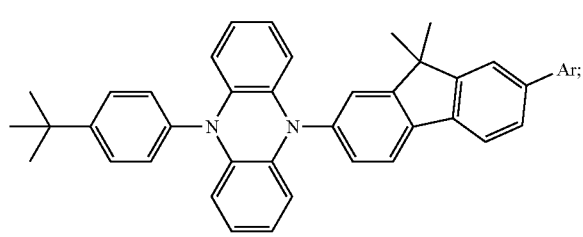

wherein Ar is an aromatic group having 6 to 60 carbon atoms or a heteroaromatic group having 6 to 60 carbon atoms.

In one embodiment, a structure of the organic compound comprises any one or a combination of the following:

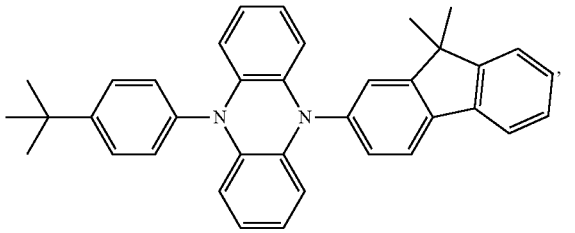

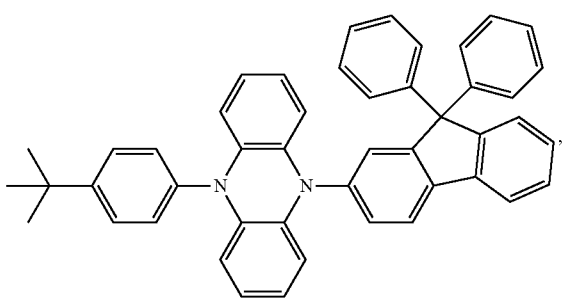

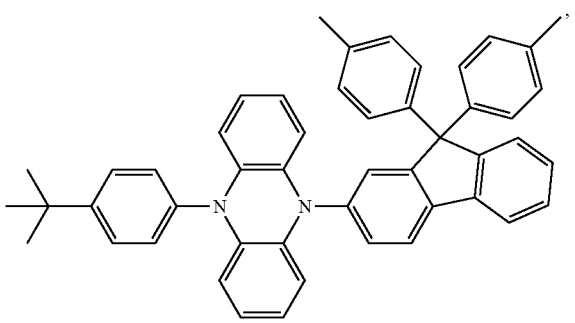

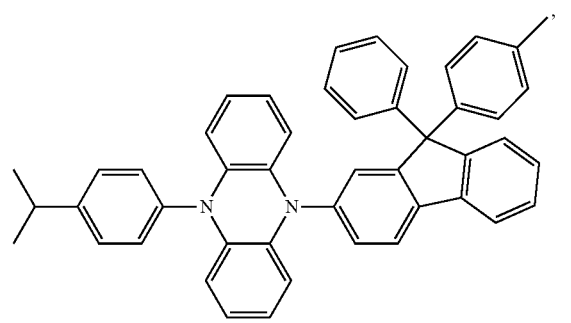

-continued
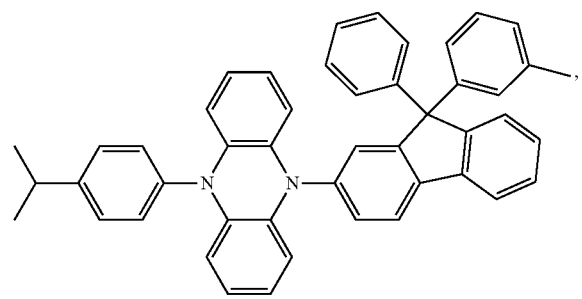
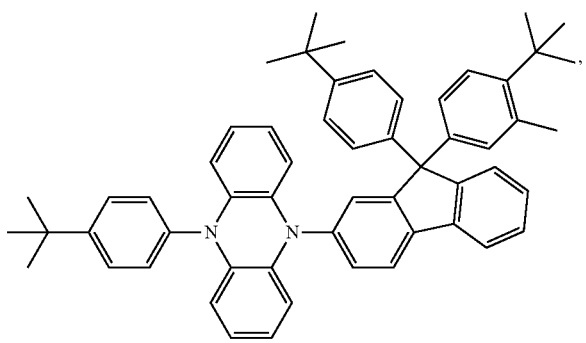
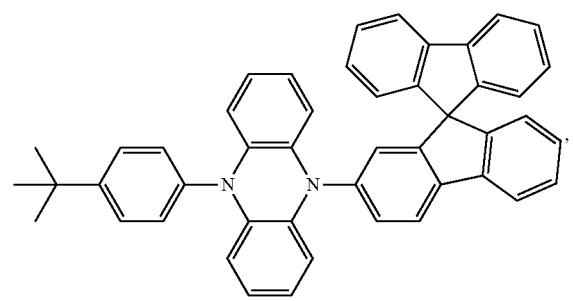
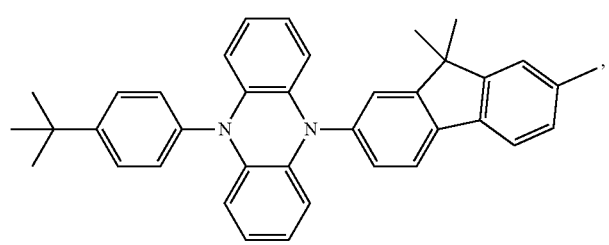
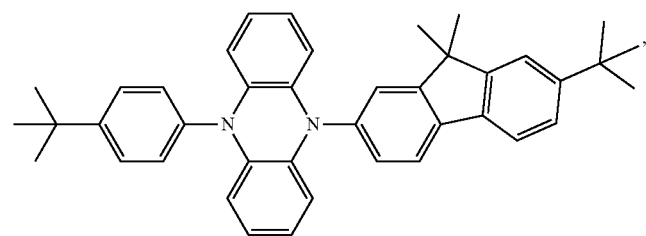
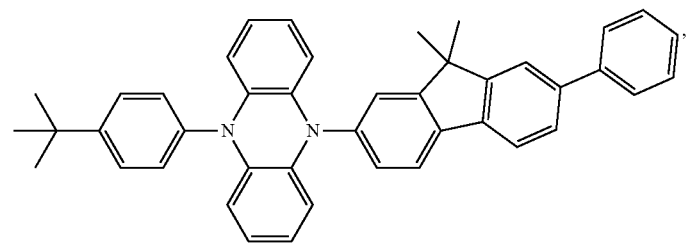
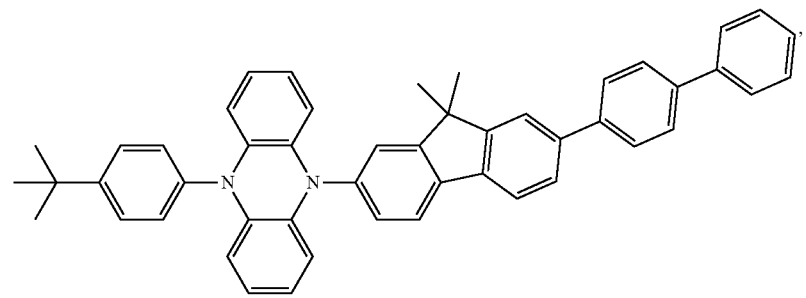
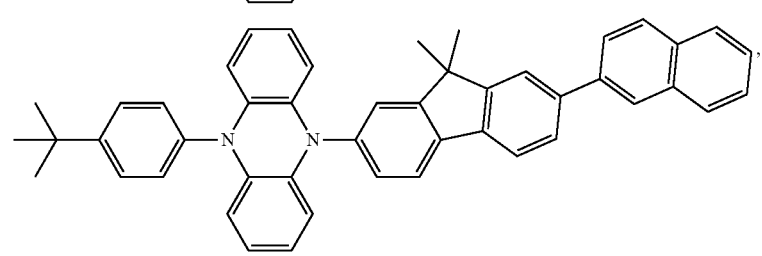

-continued
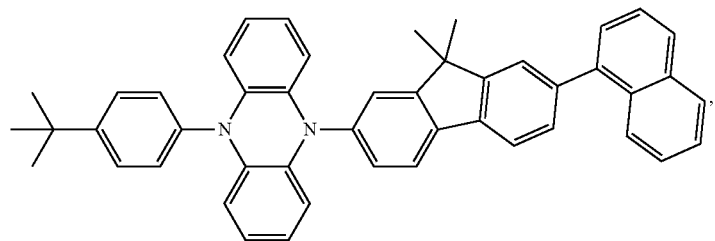
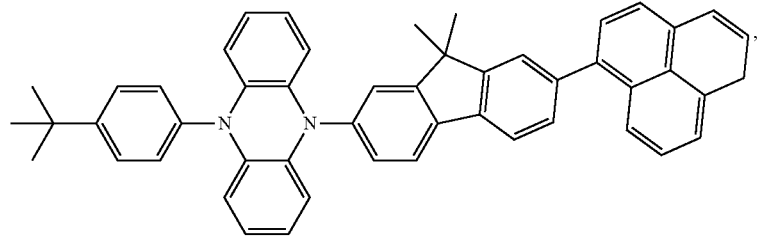
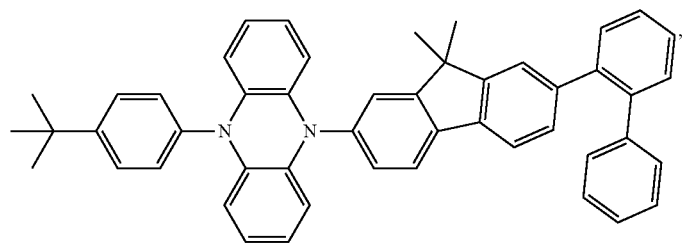
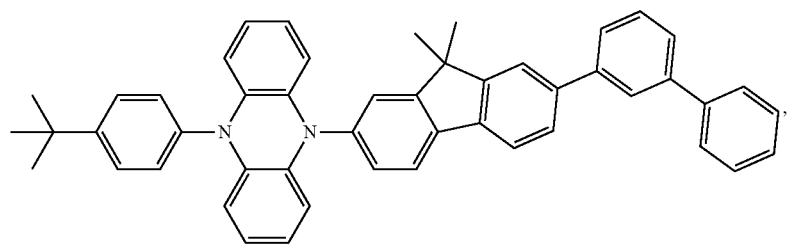
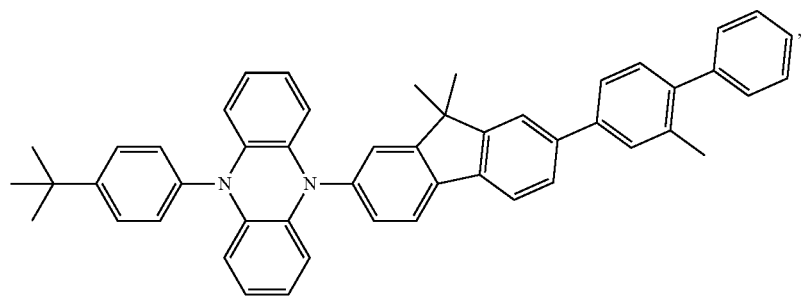
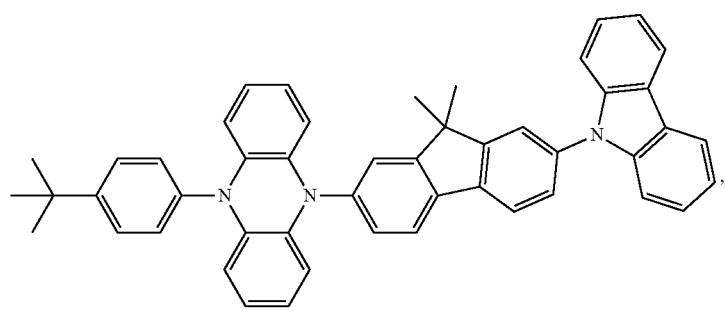

-continued

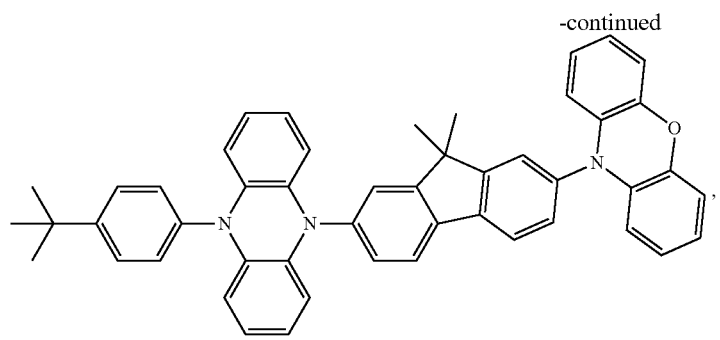

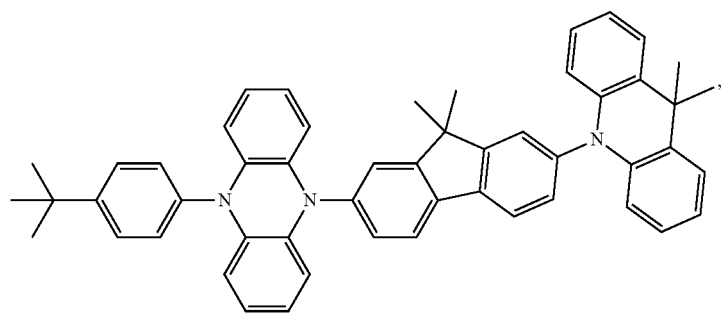

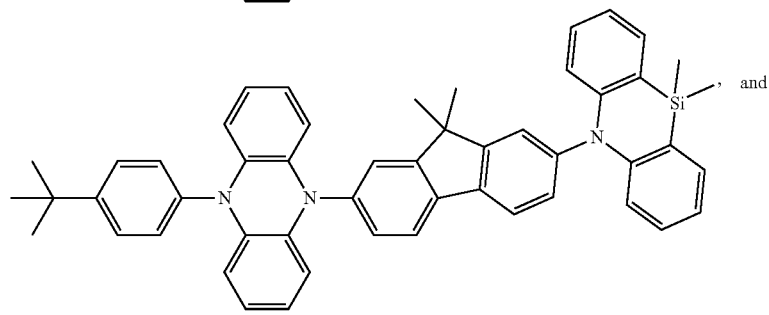, and

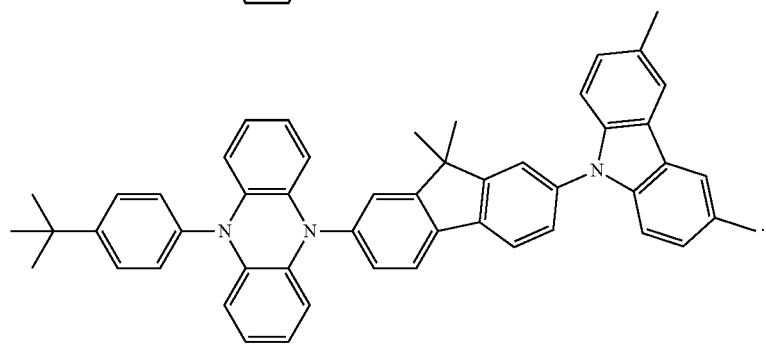

In the embodiments of the present invention, by adding other groups on the basis of a phenazine-fused fluorene structure, organic compounds with high mobility are obtained, which enhance display performance of a display device.

DETAILED DESCRIPTION OF PREFERRED EMBODIMENTS

Figure 1:
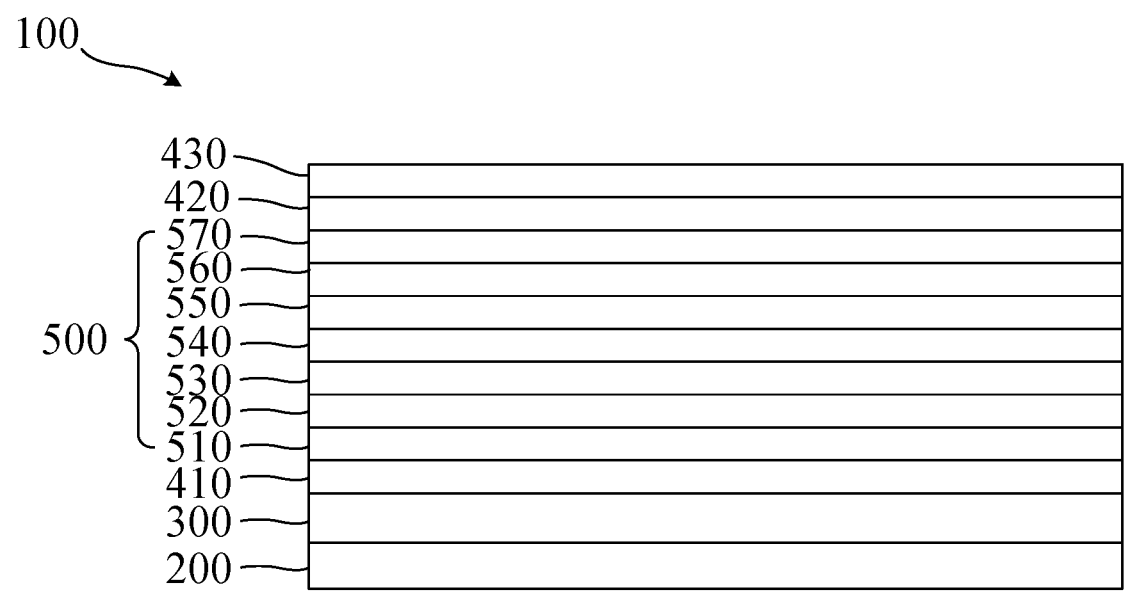
FIG. 1 is a schematic structural diagram of a display panel provided by an embodiment of the present invention.

The present application provides an organic compound, a preparation method thereof, and a display panel. In order to make the purpose, technical solution, and effect of the present application clearer and more definite, the present application is further described in detail below with reference to the accompanying drawings and examples. It should be understood that the specific embodiments described herein are only used to explain the present application, and are not used to limit the present application.

Embodiments of the present application provide an organic compound and a preparation method thereof, and a display panel, which are described in detail respectively. It should be noted that the order of description in the following embodiments is not as a limitation on the preferred order of the embodiments.

An embodiment of the present invention provides an organic compound, and the organic compound is represented by the following general formula:

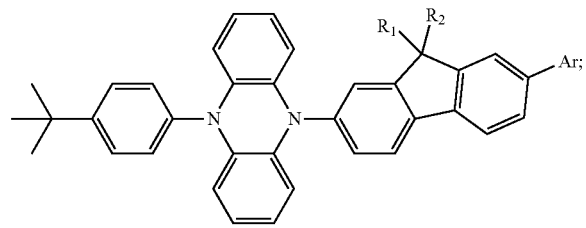

wherein Ar1 comprises any one or a combination of hydrogen, an isotope of hydrogen, an aromatic group, an arylamine group, a heteroarylamine group, and a fused ring group; and R1 and R2 are each independently any one or a combination of alkyl, alkoxy, heteroalkyl, and an aromatic group.

In the embodiments of the present invention, by adding other groups on the basis of a phenazine-fused fluorene structure, organic compounds with high mobility are obtained, which enhance display performance of a display device.

The technical solutions of the present application will now be described in conjunction with specific embodiments.

The organic compound is represented by the following general formula:

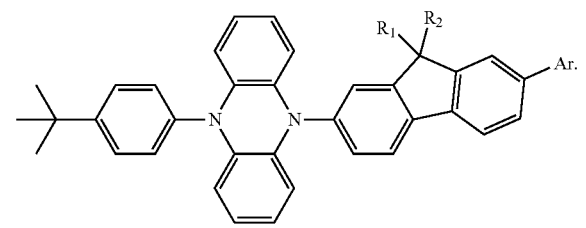

In this embodiment, the general formula is the general structural formula of a phenazine-fused fluorene-based structure.

In this embodiment, R1, R2, and Ar can all be electron-donating groups. Through the strong electron-donating ability of phenazine-fused fluorene, in combination with other electron-donating groups, a compound of high mobility is obtained, the compound can be made into a transmission material for use in light-emitting materials to enhance display efficiency of the display device.

In this embodiment, Ar comprises any one or a combination of hydrogen, an isotope of hydrogen, an aromatic group, an arylamine group, a heteroarylamine group, and a fused ring group; and R1 and R2 are each independently any one or a combination of alkyl, alkoxy, heteroalkyl, and an aromatic group. Ar has an effect of adjusting the transmission efficiency, and R1 or R2 is used to assist in adjusting the transmission efficiency.

In this embodiment, R1 or R2 is any one or a combination of an alkyl group having 1 to 22 carbon atoms, an alkoxy group having 1 to 22 carbon atoms, a heteroalkyl group having 1 to 22 carbon atoms, and an aromatic group having 6 to 60 carbon atoms. Ar comprises any one or a combination of protium, deuterium, tritium, an aromatic group having 6 to 60 carbon atoms, an arylamine group having 6 to 60 carbon atoms, a heteroarylamine group having 6 to 60 carbon atoms, and a fused ring group having 10 to 60 carbon atoms. The organic compound may be used as evaporation coating materials, C is a carbon atom, the greater the number of carbon atoms, the greater the molecular weight, the less conducive to evaporation coating, and mass production of evaporation coated molecules requires a molecular weight of the organic compound to be less than 1000.

In this embodiment, Ar includes a nitrogen-containing aromatic group or a nitrogen-containing heteroaromatic group, wherein the nitrogen element can make the organic compound has a strong electron donating ability to improve mobility performance of the organic compound.

In this embodiment, Ar is an axisymmetric group containing a benzene ring. The axisymmetric group containing a benzene ring can strengthen the stability of the organic compound through the axisymmetric property of the groups.

In this embodiment, the aromatic group includes an oxygen-containing aromatic group or a silicon-containing aromatic group, the arylamine group includes an oxygen-containing arylamine group or a silicon-containing arylamine group, and the fused ring group includes any one of naphthalene, anthracene, and pyrene. The incorporation of silicon or oxygen atom can increase the electron donating ability of the organic compound and improve the mobility performance of the organic compound.

In this embodiment, R1 and R2 are each independently any one of methyl, ethyl, and phenyl. The organic compound may be used as an evaporation coating material. A molecular weight of methyl, ethyl, or phenyl is relatively low, which is conducive to evaporation coating and is simple to synthesize.

In this embodiment, Ar is any one or a combination of the following groups:

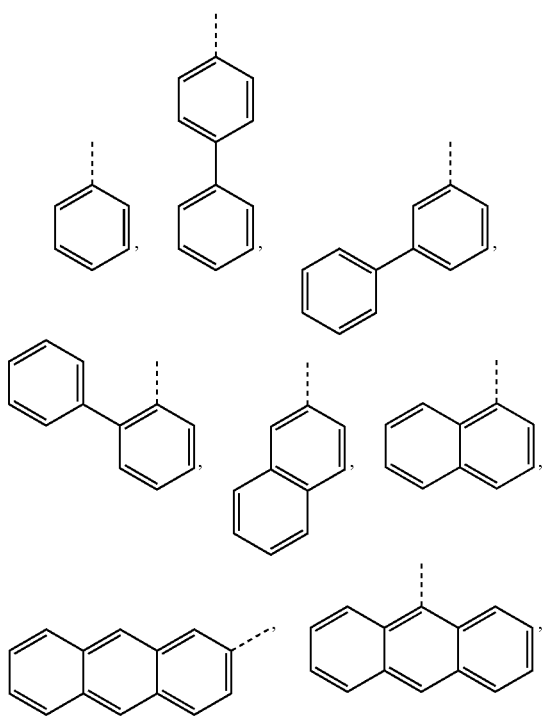

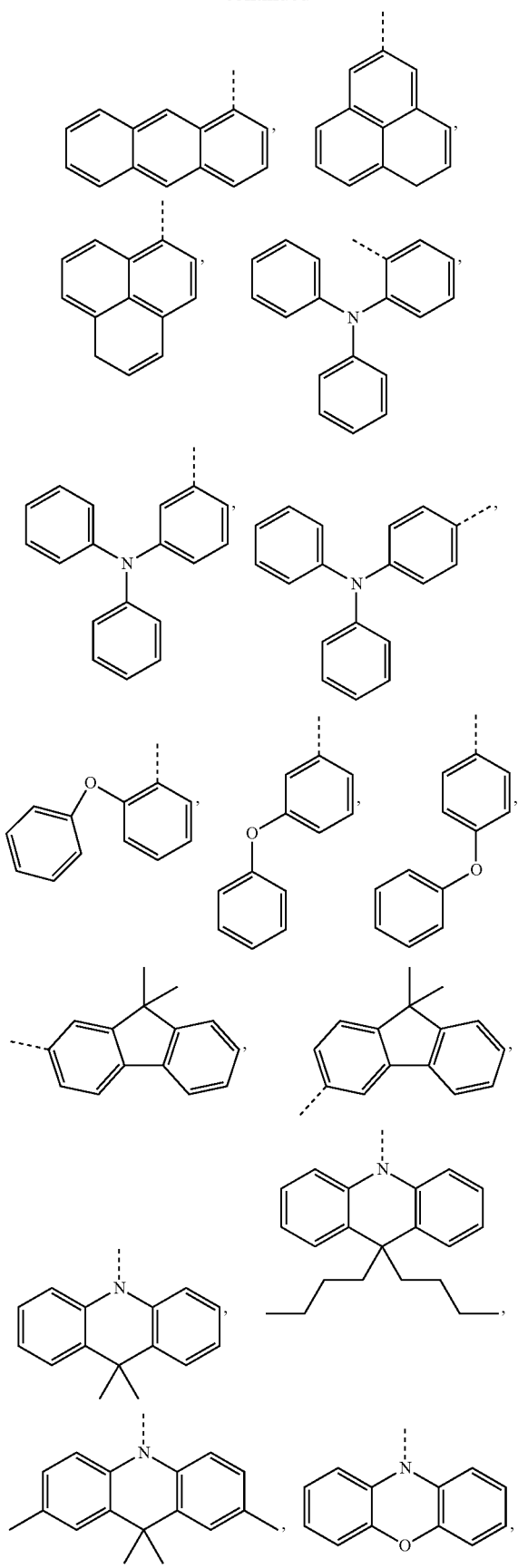
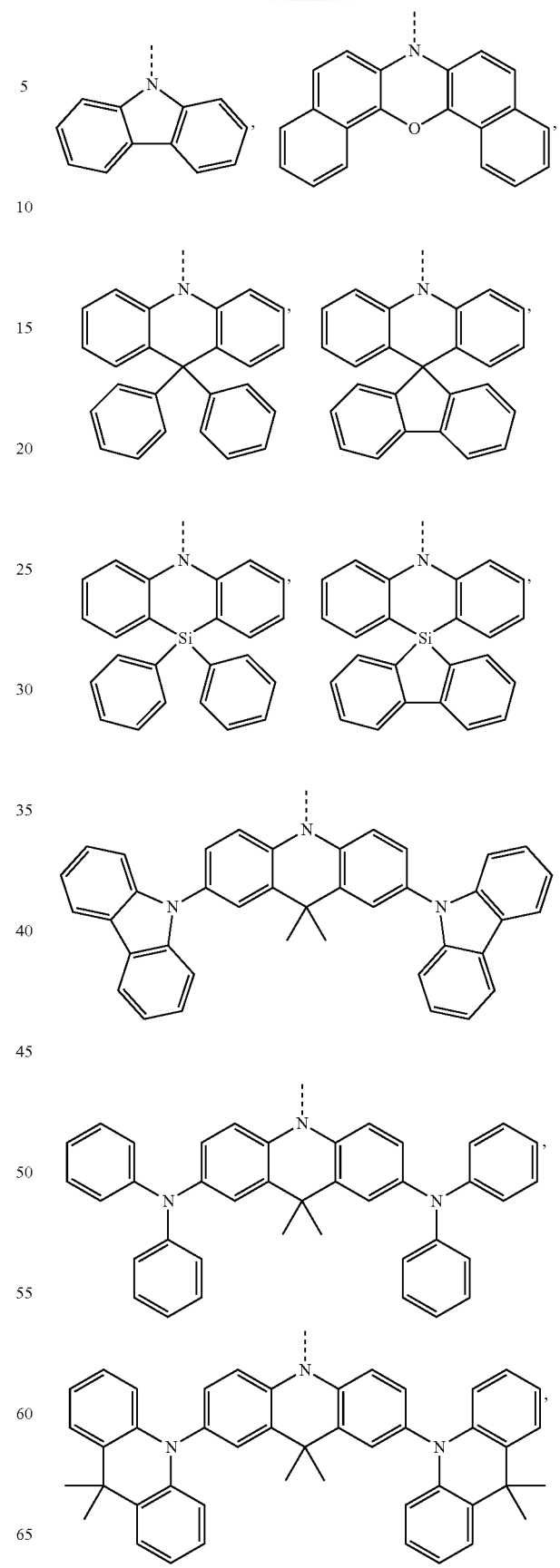

-continued

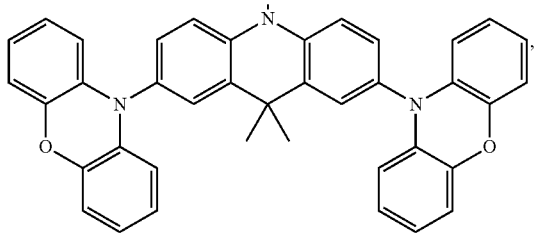

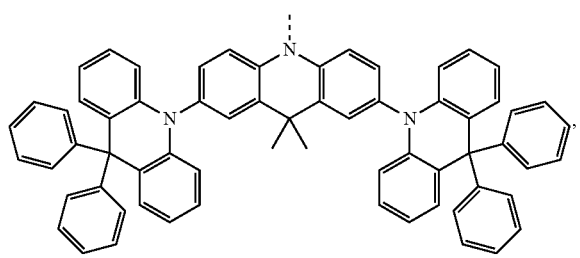

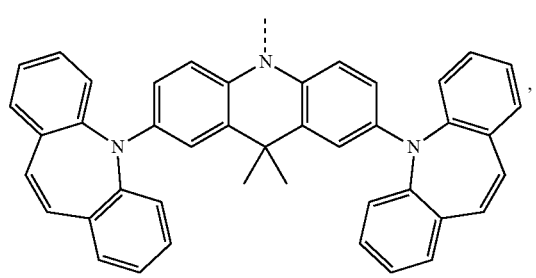

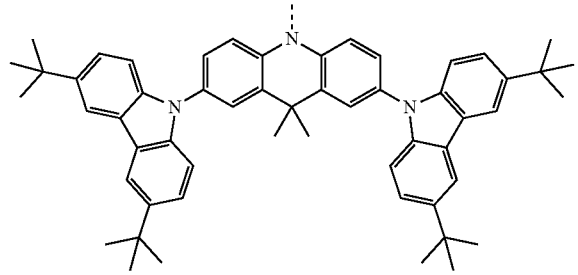

In this embodiment, Ar adjust the mobility performance of the organic compound by their different molecular weights, improve the stability of the organic compound by the symmetric groups, and improve the mobility performance of the organic compound through the nitrogen and oxygen-containing groups, as well as effectively adjust the molecular weight of the organic compound. Meanwhile, nitrogen and oxygen can form intermolecular bonds and intramolecular bonds with hydrogen and isotopes of hydrogen to further improve the stability of the organic compound. In addition, the stability of the organic compound is improved through symmetry of silicon atoms.

In this embodiment, a structural formula of the organic compound is:

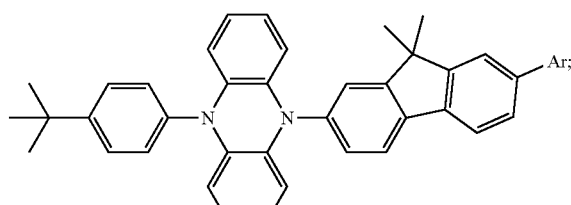

Ar is an aromatic group with 6 to 60 carbon atoms or a heteroaromatic group with 6 to 60 carbon atoms. It can be seen that both R1 and R2 are methyl groups, and the methyl group has a low molecular weight, which is thereby conducive to evaporation coating, reduces the difficulty of synthesis, and the main design direction for synthesis scheme is focused on Ar to improve the mobility performance of the organic compound.

In this embodiment, a structure of the organic compound includes any one or a combination of the following:

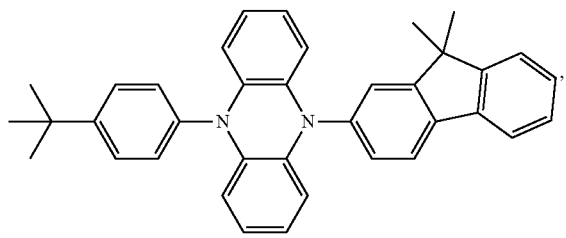

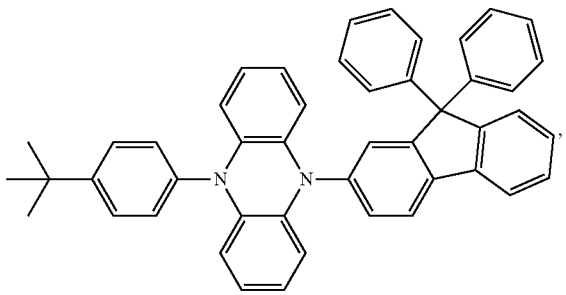

-continued
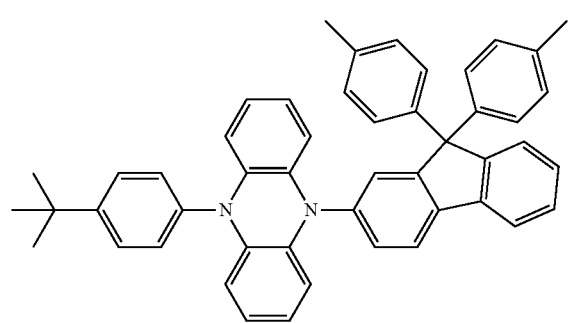
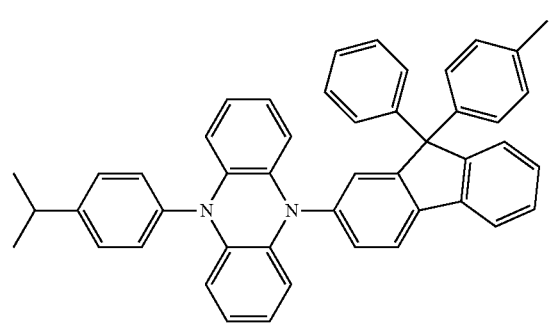
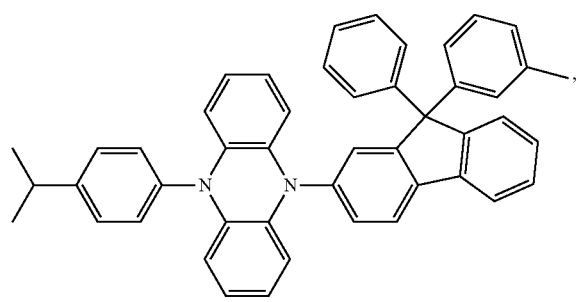
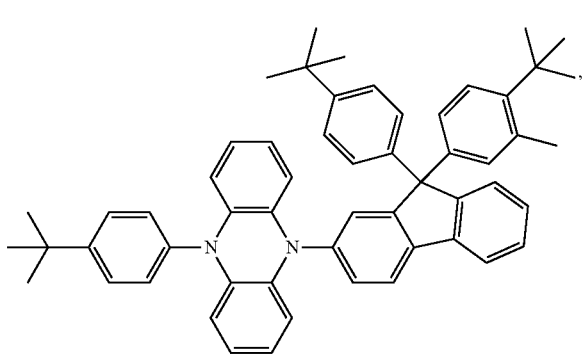
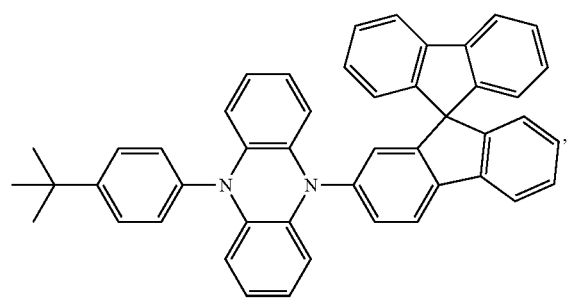
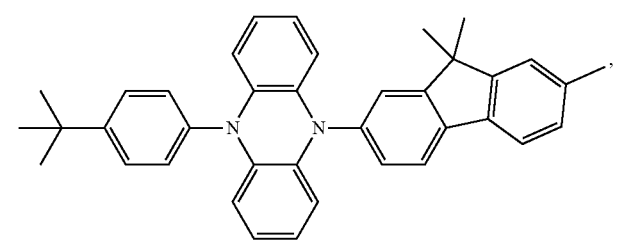
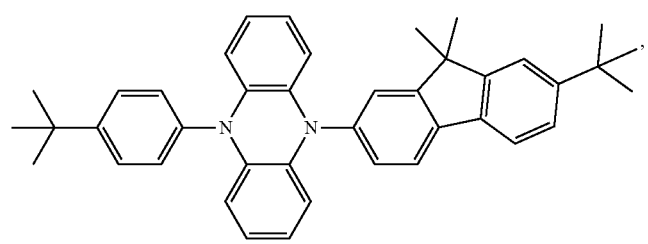
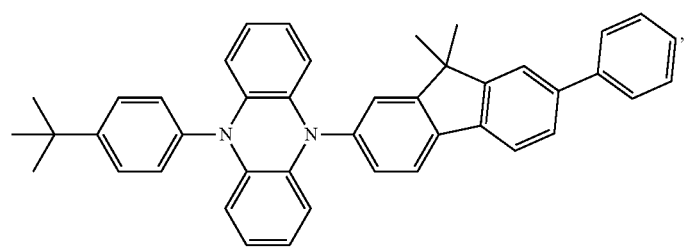

-continued
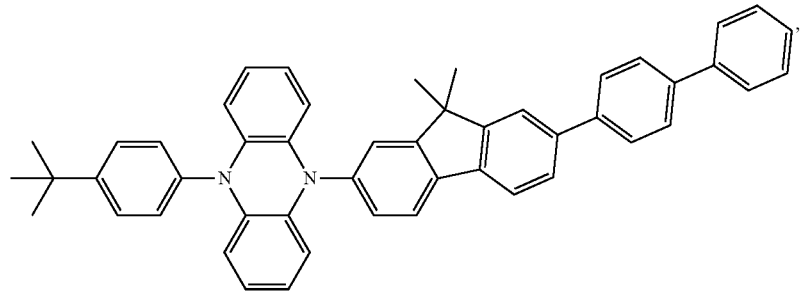
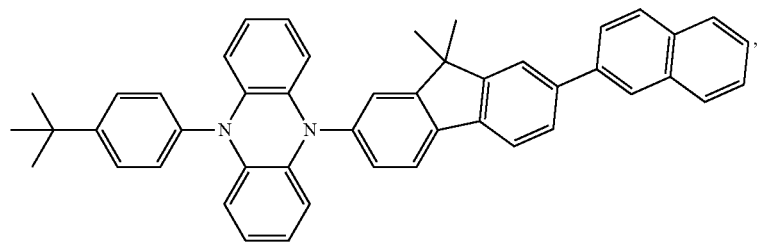
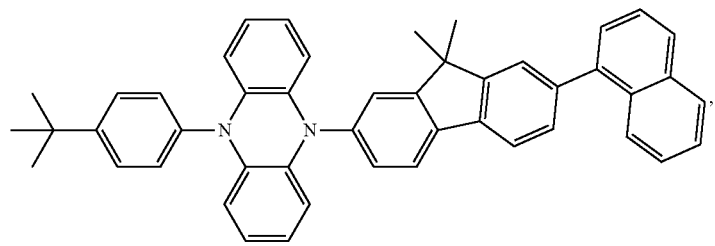
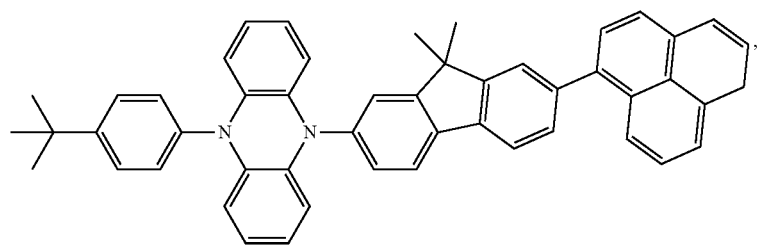
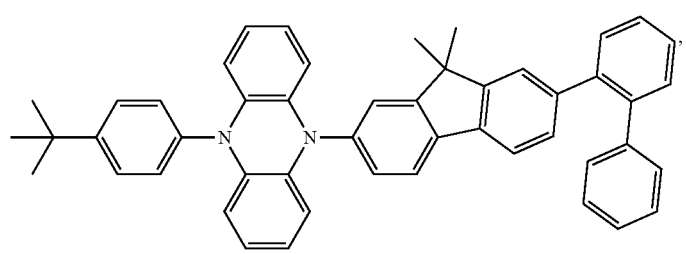
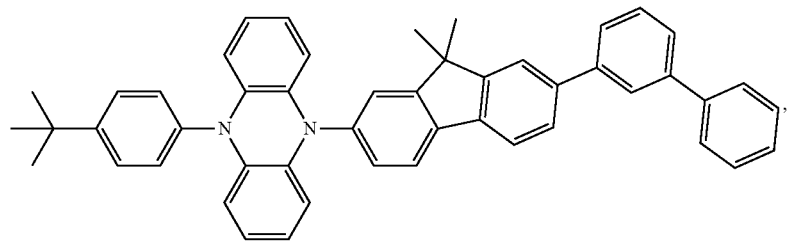

-continued
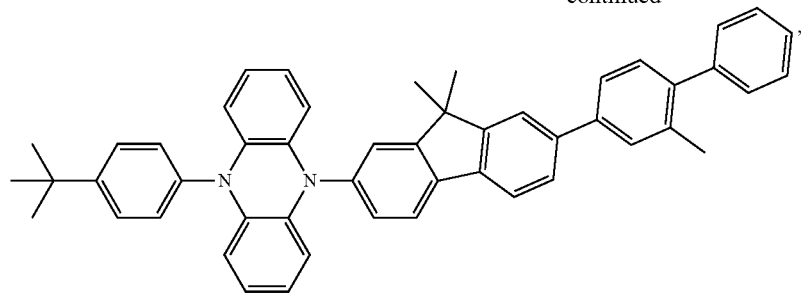
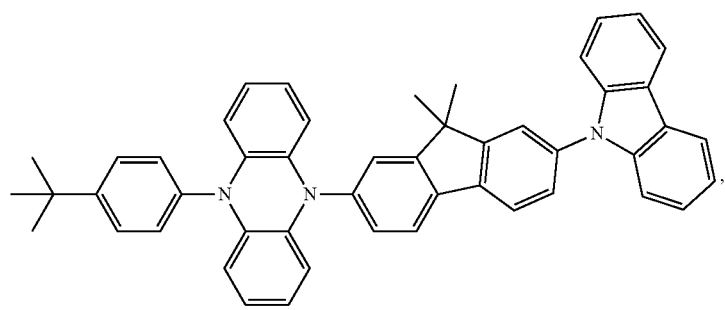
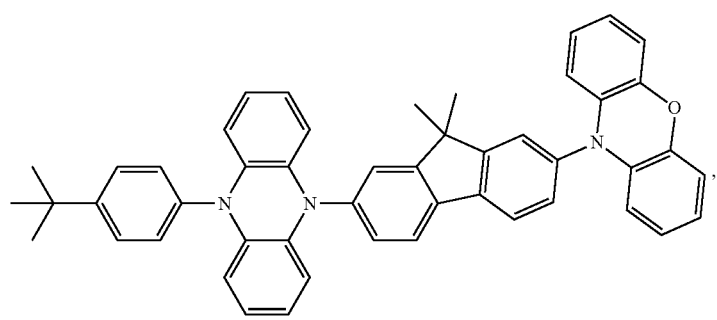
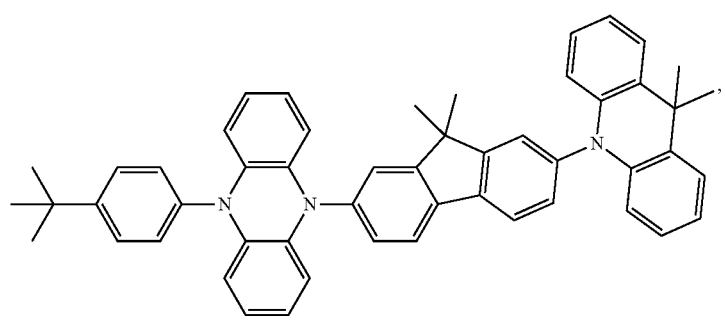
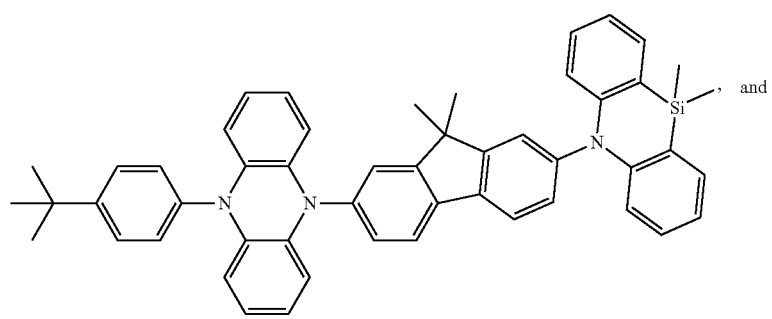

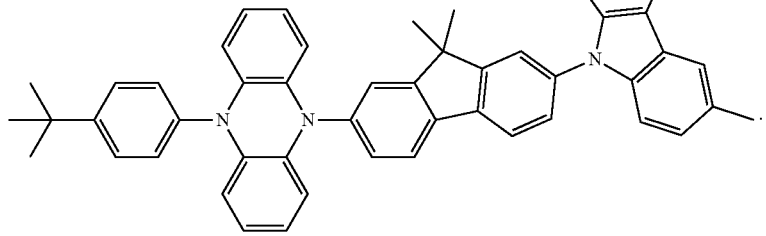

as examples, the three compounds are named Compound 1, Compound 2, and Compound 3.

In this example, the HOMO electrochemical energy level of Compound 1 is −5.58 eV, and the LUMO electrochemical energy level is −2.43 eV. The HOMO electrochemical energy level of Compound 2 is −5.61 eV, and the LUMO electrochemical energy level is −2.54 eV. The HOMO electrochemical energy level of Compound 3 is −5.66 eV, and the LUMO electrochemical energy level is −2.44 eV. It can be seen that taking the three structures as examples, characterization parameters indicate that the organic compounds can be used as transporting materials In the embodiments of the present invention, by adding other groups on the basis of a phenazine-fused fluorene structure, organic compounds with high mobility are obtained, which enhance display performance of a display device.

An embodiment of the present invention also provides a method of preparing an organic compound, including:

S100, mixing a first material and a second material to form the organic compound, and the organic compound is represented by the general formula (1):

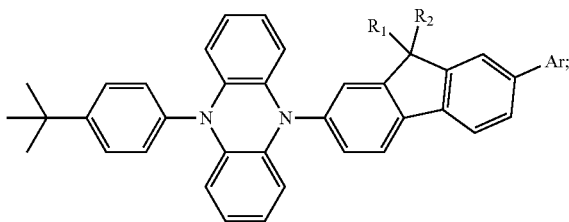

the first material is represented by the general formula (2):

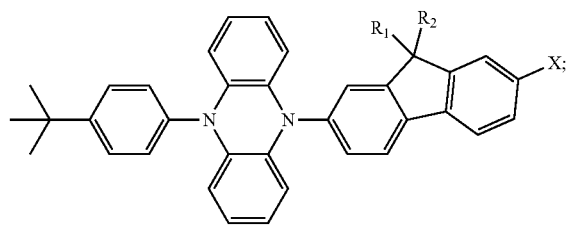

wherein R1 and R2 are each independently any one or a combination of alkyl, alkoxy, heteroalkyl, and an aromatic group; X is a halogen, and the second material comprises any one or a combination of an aromatic group, an arylamine group, a heteroarylamine group, and a fused ring group; and Ar comprises any one or a combination of hydrogen, an isotope of hydrogen, an aromatic group, an arylamine group, and a heteroarylamine group.

In the embodiments of the present invention, by adding other groups on the basis of a phenazine-fused fluorene structure, organic compounds with high mobility are obtained, which enhance display performance of a display device.

The technical solutions of the present invention will now be described in conjunction with specific embodiments.

The method of preparing the organic compound includes:

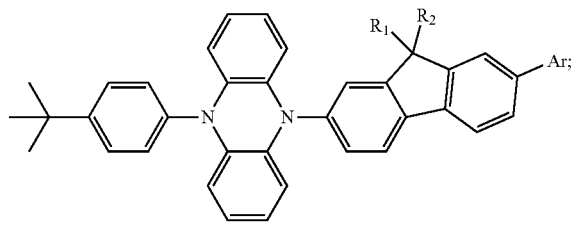

the first material is represented by the general formula (2):

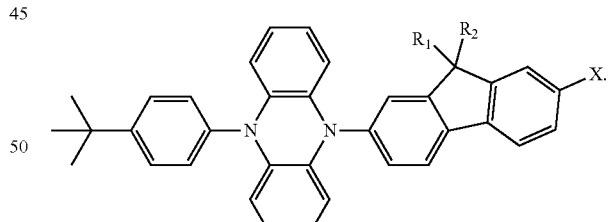

In this embodiment, R1, R2, and Ar can all be electron-donating groups. Through the strong electron-donating ability of phenazine-fused fluorene, in combination with other electron-donating groups, a compound of high mobility is obtained, the compound can be made into a transmission material for use in light-emitting materials to enhance display efficiency of the display device.

In this embodiment, Ar comprises any one or a combination of hydrogen, an isotope of hydrogen, an aromatic group, an arylamine group, a heteroarylamine group, and a fused ring group; and R1 and R2 are each independently any one or a combination of alkyl, alkoxy, heteroalkyl, and an aromatic group. Ar has an effect of adjusting the transmission efficiency, and R1 or R2 is used to assist in adjusting the transmission efficiency.

In this embodiment, R1 and R2 are each independently any one or a combination of alkyl, alkoxy, heteroalkyl, and an aromatic group; X is a halogen, and the second material comprises any one or a combination of an aromatic group, an arylamine group, a heteroarylamine group, and a fused ring group; and Ar comprises any one or a combination of hydrogen, an isotope of hydrogen, an aromatic group, an arylamine group, and a heteroarylamine group.

In this embodiment, the second material also includes a dehydrogenation hydrogenation agent, or the X in the first material is hydrogen.

In this embodiment, the dehalogenation hydrogenation agent may include $LiAlH_4$, or tri-tert-butylstannane. Alternatively, in an inorganic alkaline environment, a soluble organic carrying palladium complex is used as a catalyst for hydrodehalogenation.

In this embodiment, X is bromine, iodine, or chlorine. In terms of synthesis efficiency, the synthesis efficiency of bromine and iodine is higher; and in terms of cost calculation, the cost of chlorine is lower.

In this embodiment, R1 or R2 is any one or a combination of an alkyl group having 1 to 22 carbon atoms, an alkoxy group having 1 to 22 carbon atoms, a heteroalkyl group having 1 to 22 carbon atoms, and an aromatic group having 6 to 60 carbon atoms. Ar comprises any one or a combination of protium, deuterium, tritium, an aromatic group having 6 to 60 carbon atoms, an arylamine group having 6 to 60 carbon atoms, a heteroarylamine group having 6 to 60 carbon atoms, and a fused ring group having 10 to 60 carbon atoms. The organic compound may be used as evaporation coating materials, C is a carbon atom, the greater the number of carbon atoms, the greater the molecular weight, the less conducive to evaporation coating, and mass production of evaporation coated molecules requires a molecular weight of the organic compound to be less than 1000.

In this embodiment, Ar includes a nitrogen-containing aromatic group or a nitrogen-containing heteroaromatic group, wherein the nitrogen element can make the organic compound has a strong electron donating ability to improve mobility performance of the organic compound.

In this embodiment, Ar is an axisymmetric group containing a benzene ring. The axisymmetric group containing a benzene ring can strengthen the stability of the organic compound through the axisymmetric property of the groups.

In this embodiment, the aromatic group includes an oxygen-containing aromatic group or a silicon-containing aromatic group, the arylamine group includes an oxygen-containing arylamine group or a silicon-containing arylamine group, and the fused ring group includes any one of naphthalene, anthracene, and pyrene. The incorporation of silicon or oxygen atom can increase the electron donating ability of the organic compound and improve the mobility performance of the organic compound.

In this embodiment, R1 and R2 are each independently any one of methyl, ethyl, and phenyl. The organic compound may be used as an evaporation coating material. A molecular weight of methyl, ethyl, or phenyl is relatively low, which is conducive to evaporation coating and is simple to synthesize.

In this embodiment, Ar is any one or a combination of the following groups:

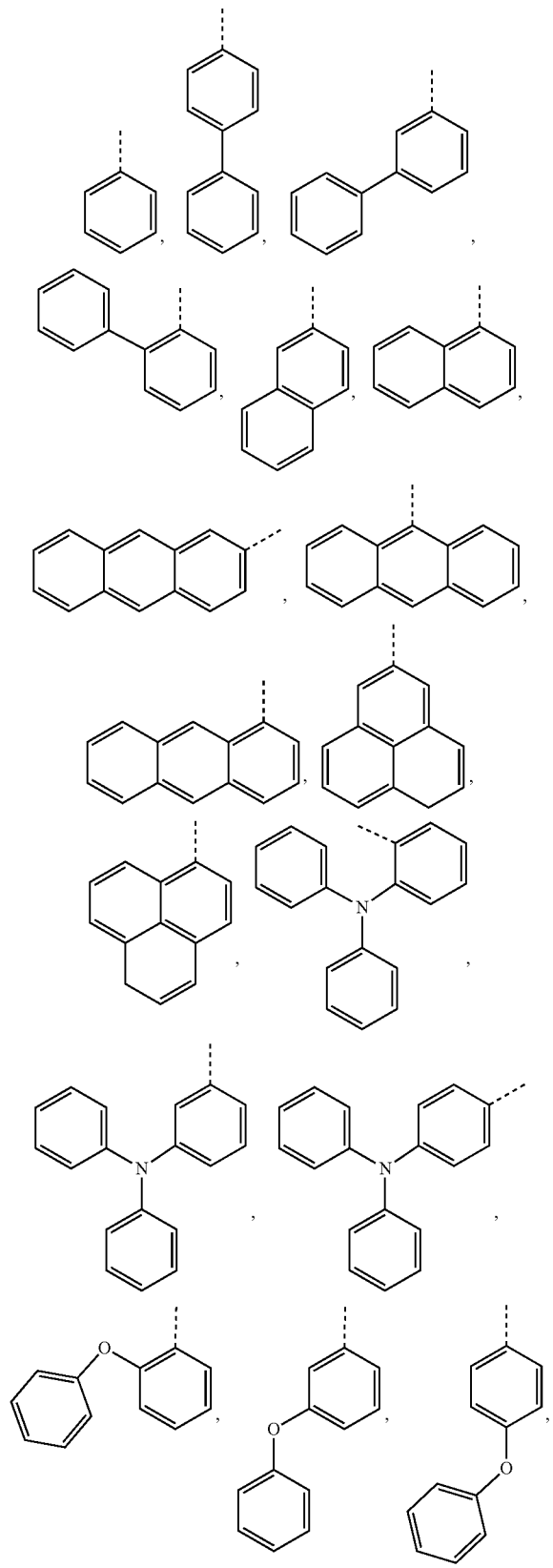

-continued
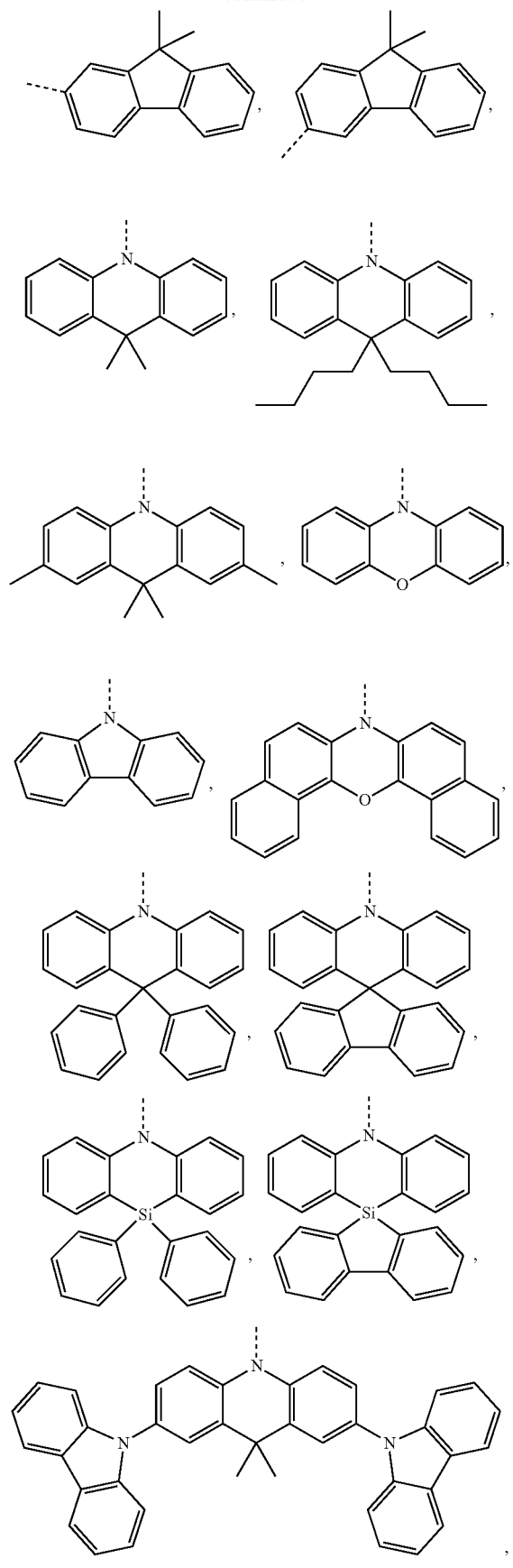
-continued
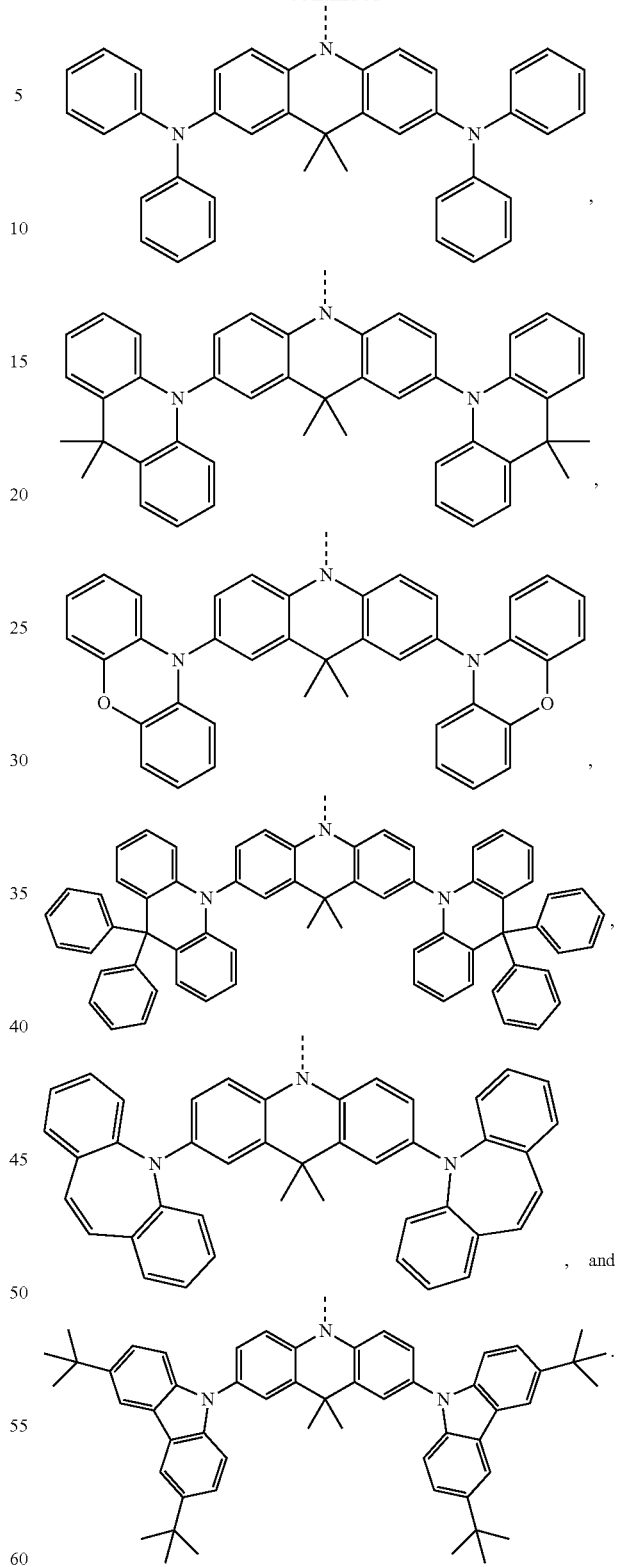
In this embodiment, Ar adjust the mobility performance of the organic compound by their different molecular weights, improve the stability of the organic compound by the symmetric groups, and improve the mobility performance of the organic compound through the nitrogen and oxygen-containing groups, as well as effectively adjust the molecular weight of the organic compound. Meanwhile, nitrogen and oxygen can form intermolecular bonds and intramolecular bonds with hydrogen and isotopes of hydrogen to further improve the stability of the organic compound. In addition, the stability of the organic compound is improved through symmetry of silicon atoms.

In this embodiment, a structural formula of the organic compound is:

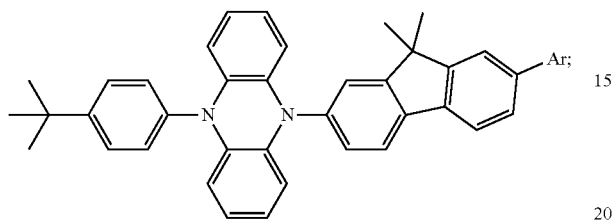

Ar is an aromatic group with 6 to 60 carbon atoms or a heteroaromatic group with 6 to 60 carbon atoms. It can be seen that both R1 and R2 are methyl groups, and the methyl group has a low molecular weight, which is thereby conducive to evaporation coating, reduces the difficulty of synthesis, and the main design direction for synthesis scheme is focused on Ar to improve the mobility performance of the organic compound.

In this embodiment, a structural formula of the first material is:

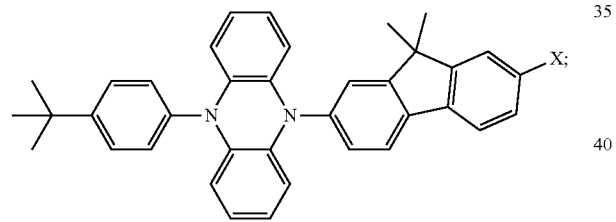

the second material includes any one of the following groups:

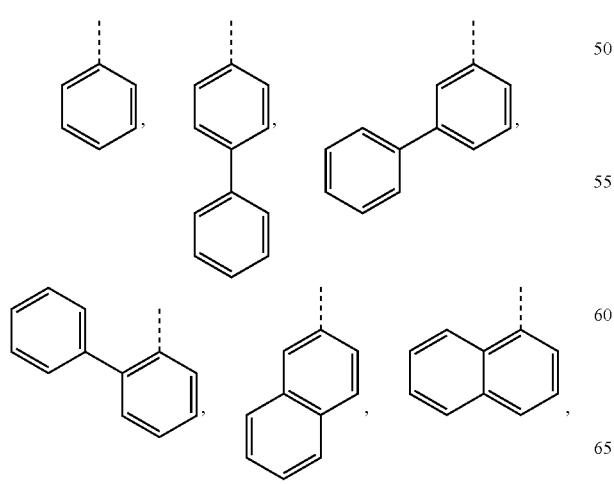

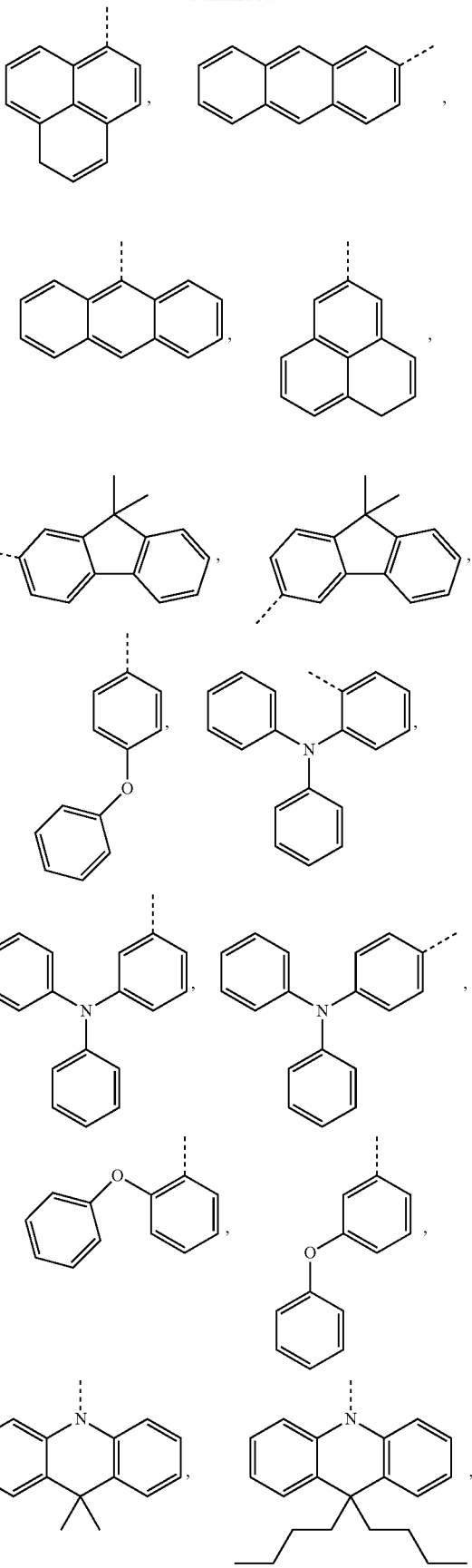

-continued

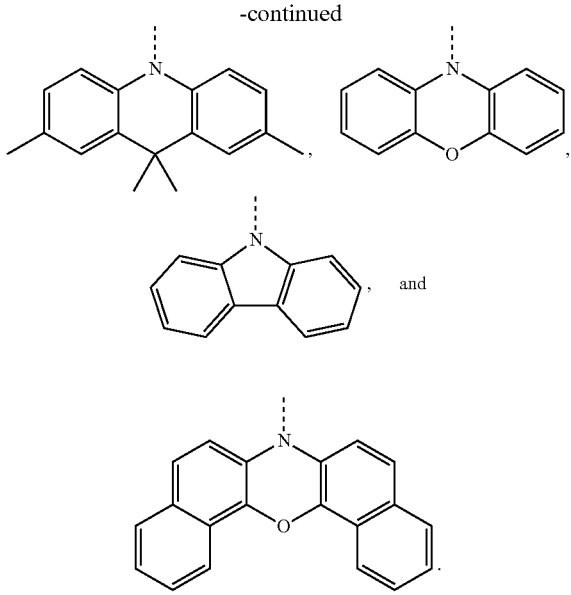

In this embodiment, the step S100 is in an inert gas environment for reaction, and the inert gas environment can be argon, or helium, which can protect the stability of the organic compound and ensure the efficiency of synthesis.

In this embodiment, the step S100 includes the following steps:

S110, mixing the first material and the second material in a molar ratio of 1:1 to 1:1.3 to form a first mixture.

In this embodiment, the step S110 is to mix the first material and the second material in a molar ratio of 1:1.2 to form a first mixture. Appropriately increasing the ratio of the second material can increase utilization rate of the first material. When the first material and the second material are mixed in a molar ratio of 1:1.2, they can be fully reacted, and it can also avoid the waste of the second substance or the excessive impurities in the product causing product purity not up to standard.

S120, adding a catalyst to the first mixture.

In this embodiment, the catalyst can speed up the progress of the step S100 to improve the production efficiency of the organic compound.

In this embodiment, the catalyst may be palladium acetate. Palladium acetate can speed up the reaction without undermining the performance of the organic compound. It is also easier to separate the palladium acetate in the later stage, which is convenient and quick, and accelerates the production efficiency of the reaction.

In this embodiment, a ratio of an amount of the catalyst material to the amount of the first material is 1:20 to 1:30.

In this embodiment, the ratio of the amount of the material of the catalyst to the amount of the material of the first material is 1:25. This content can not only ensure the catalytic efficiency, but also facilitate the separation and improve the production efficiency during the later purification and separation of the catalyst.

S130, adding a ligand to the first mixture.

In this embodiment, the ligand can be used to protect other functional groups or stabilize some easily reactive compounds, such as any one or more of aromatic groups, arylamine groups, heteroarylamine groups and fused ring groups of the second material, as well as R1, R2, and the nitrogen heterocyclic ring in the first material.

In this embodiment, the ligand can be tri-tert-butyl phosphine tetrafluoroborate. Using tri-tert-butyl phosphine tetrafluoroborate as the ligand, the reaction conditions do not require an addition of expensive silver salt, which can save steps to speed up the synthesis of complex polyaromatic ring compounds, make the reaction more green and environmentally friendly and have high atom utilization, and realize the currently advocated concept of green chemistry, as well as be contribute to functional group compatibility and reaction efficiency.

In this embodiment, the ratio of the amount of the ligand material to the amount of the second material is 1:8 to 1:12.

In this embodiment, the ratio of the amount of the ligand material to the amount of the second material is 1:10. This content can not only ensure that the group protecting the second material will not be damaged, but also can prevent the excessive content of the ligand from inhibiting the progress of the reaction, thus ensuring the efficiency of reaction production.

S140, adding alkali to the first mixture.

In this embodiment, the alkali is used to provide an alkaline environment. The alkali may be NaOt-Bu, NaOt-Bu, not only provides an alkaline environment, but also has a certain catalytic effect to speed up the production efficiency of the organic compound.

In this embodiment, a ratio of an amount of the alkali material to an amount of the second material is 1:0.8 to 1:1.2.

In this embodiment, the ratio of the amount of the alkali material to the amount of the second material is 1:1. This content can not only ensure existence of an alkaline environment, but also increase a certain reaction rate and ensure the efficiency of the production reaction, and at the same time will not make the organic compound too viscous due to excessively high alkalinity, which is inconvenient for subsequent steps.

S150, adding dehydrated and deoxygenated toluene to the first mixture.

In this embodiment, the step S110 to the step S150 can be performed simultaneously.

In this embodiment, after the step S110 to the step S150, a second mixture is formed.

S160, the second mixture is reacted at 120° C. for 24 hours to form a third mixture.

S170, cooling the third mixture to room temperature.

S180, extracting the third mixture in ice water and combining its organic phases to form a fourth mixture.

In this embodiment, an extractant used in the step S180 may be dichloromethane.

S190, the fourth mixture is subjected to rotary evaporation, column chromatography separation and purification to prepare the organic compound.

In this embodiment, the column chromatography agent for column chromatography can be dichloromethane:n-hexane in a volume ratio of 1:1 to 1:10.

In this embodiment, the column chromatography agent for column chromatography can be dichloromethane:n-hexane in a volume ratio of 1:5. It can achieve good separation effects without excessive waste and save production costs.

In this embodiment, a structure of the organic compound includes any one or a combination of the following:
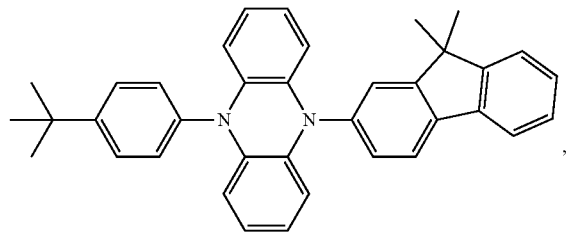
,
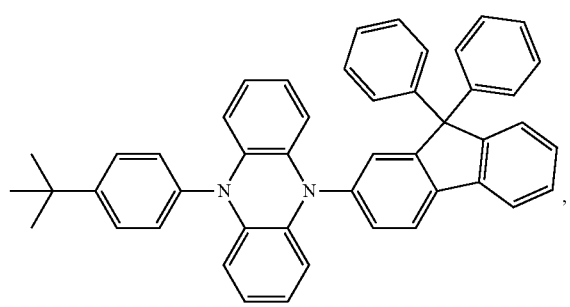
,
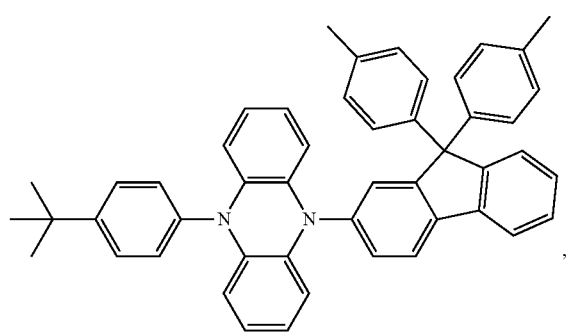
,
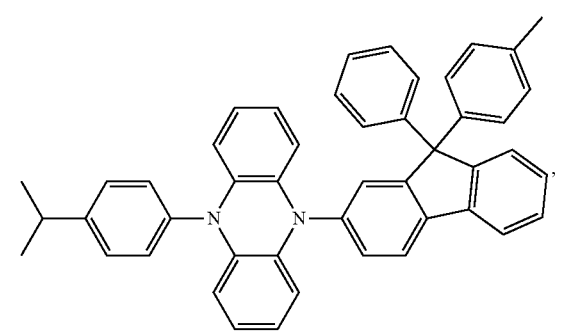
,
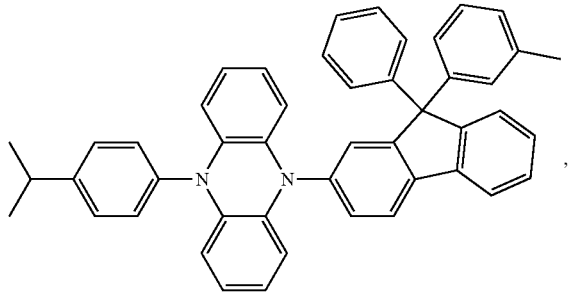
,
-continued
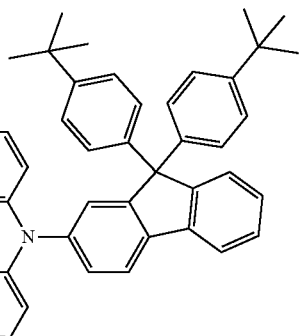
,
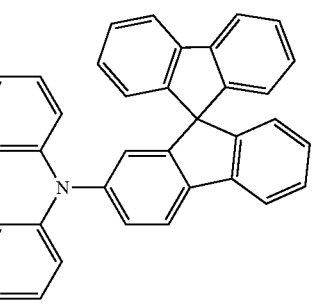
,
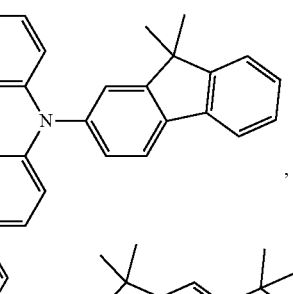
,
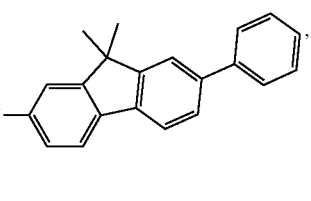
,
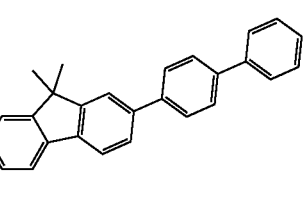
,
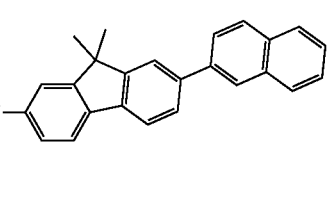
,

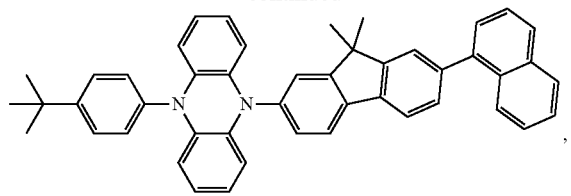
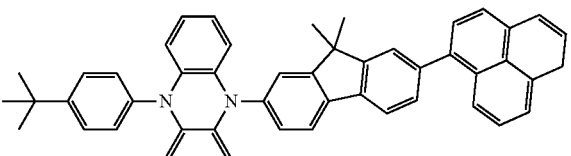
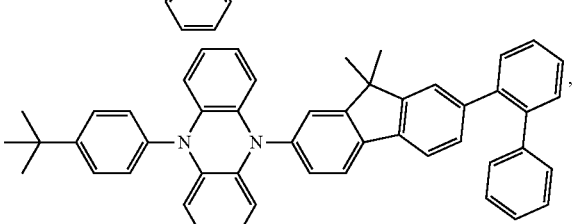
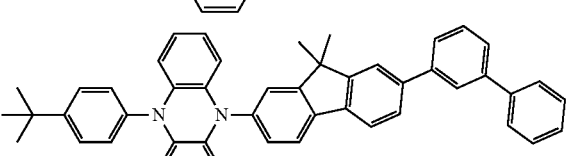
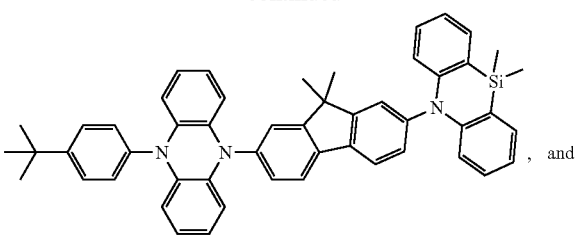
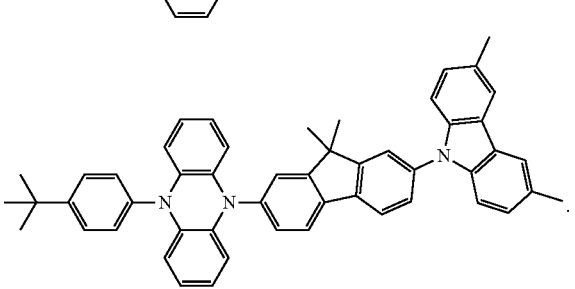

Taking

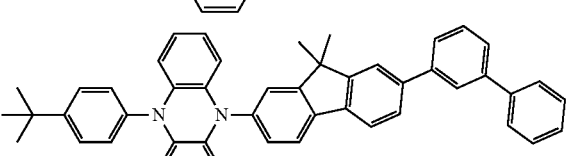
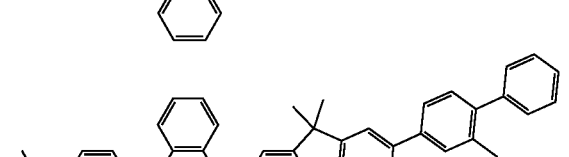
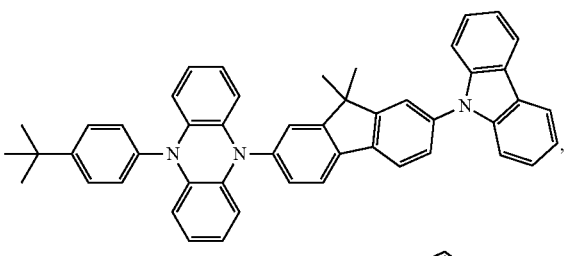
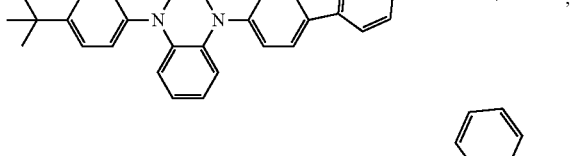
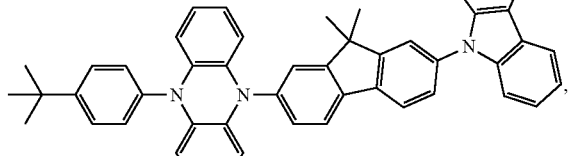
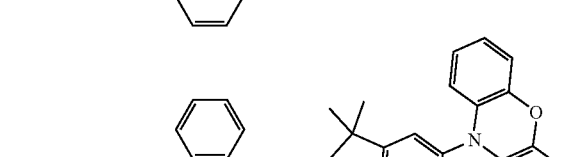
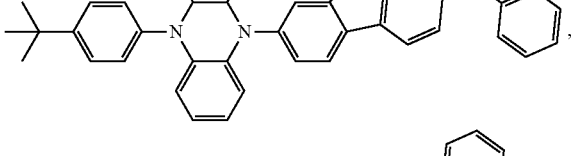
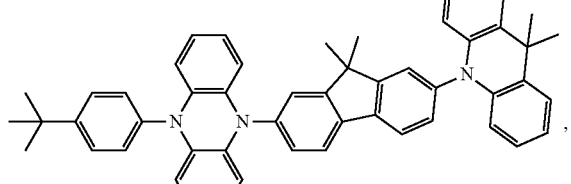

as examples, the three compounds are named Compound 1, Compound 2, and Compound 3.

In this example, the HOMO electrochemical energy level of Compound 1 is −5.58 eV, and the LUMO electrochemical energy level is −2.43 eV. The HOMO electrochemical energy level of Compound 2 is −5.61 eV, and the LUMO electrochemical energy level is −2.54 eV. The HOMO electrochemical energy level of Compound 3 is −5.66 eV, and the LUMO electrochemical energy level is −2.44 eV. It can be seen that taking the three structures as examples, characterization parameters indicate that the organic compounds can be used as transporting materials.

In this embodiment, the reaction formula of Compound 1 is as follows:

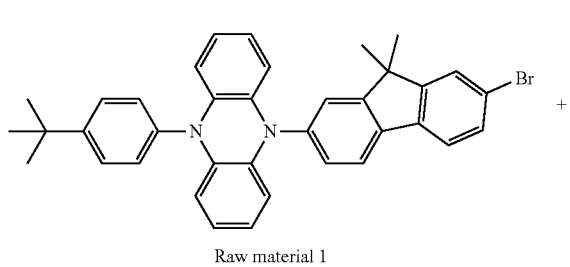

Raw material 1

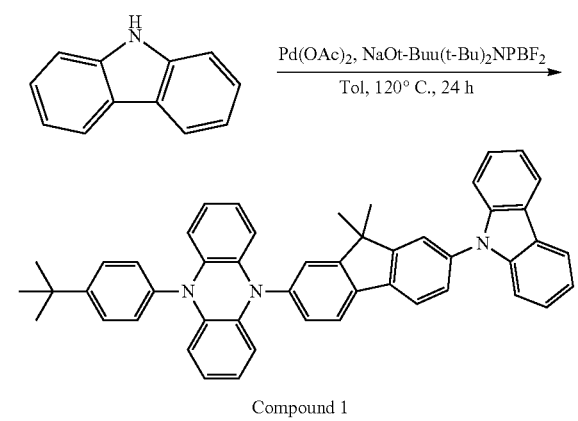

Compound 1

In this embodiment, the steps of the method of preparing Compound 1 are as follows, for example. Raw material 1 (2.92 g, 5 mmol), carbazole (1.00 g, 6 mmol), and palladium acetate (45 mg, 0.2 mmol) and tri-tert-butyl phosphine tetrafluoroborate (0.17 g, 0.6 mmol) were added to a 250 mL two-neck bottle, followed by addition of NaOt-Buu (0.58 g, 6 mmol) in a glove box. In an argon atmosphere, 100 mL of toluene that has been dewatered and deoxygenated was injected for reaction at 120° C. for 24 hours. After cooling to room temperature, the reaction solution was poured into 200 mL ice water, extracted three times with dichloromethane. The organic phases of the extract were combined, spun into silica gel, and isolated and purified by column chromatography (dichloromethane:n-hexane, v:v is 1:5) to obtain 2.3 g of white powder, MS (EI) m/z: [M]+: 671.32, with a yield of 69%.

In this embodiment, the reaction formula of Compound 2 is as follows:

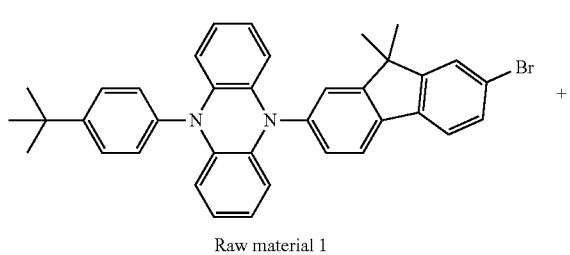

Raw material 1

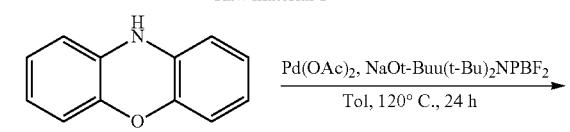

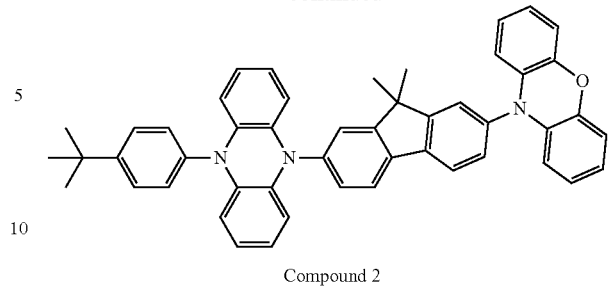

Compound 2

In this embodiment, the steps of the method of preparing Compound 2 are as follows, for example. Raw material 1 (2.92 g, 5 mmol), phenoxazine (1.10 g, 6 mmol), and palladium acetate (45 mg, 0.2 mmol) and tri-tert-butyl phosphine tetrafluoroborate (0.17 g, 0.6 mmol) were added to a 250 mL two-neck bottle, followed by addition of NaOt-Buu (0.58 g, 6 mmol) in a glove box. In an argon atmosphere, 100 mL of toluene that has been dewatered and deoxygenated was injected for reaction at 120° C. for 24 hours. After cooling to room temperature, the reaction solution was poured into 200 mL ice water, extracted three times with dichloromethane. The organic phases of the extract were combined, spun into silica gel, and isolated and purified by column chromatography (dichloromethane:n-hexane, v:v is 1:5) to obtain 2.5 g of white powder, MS (EI) m/z: [M]+: 687.30, with a yield of 73%.

In this embodiment, the reaction formula of Compound 3 is as follows:

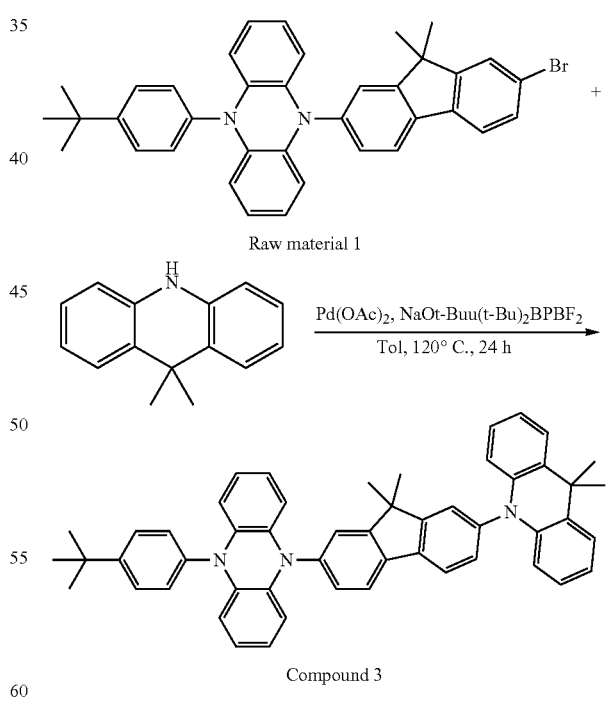

In this embodiment, the steps of the method of preparing Compound 3 are as follows, for example. Raw material 1 (2.92 g, 5 mmol), 9,9'-dimethylacridine (1.26 g, 6 mmol), and palladium acetate (45 mg, 0.2 mmol) and tri-tert-butyl phosphine tetrafluoroborate (0.17 g, 0.6 mmol) were added to a 250 mL two-neck bottle, followed by addition of NaOt-Buu (0.58 g, 6 mmol) in a glove box. In an argon atmosphere, 100 mL of toluene that has been dewatered and deoxygenated was injected for reaction at 120° C. for 24 hours. After cooling to room temperature, the reaction solution was poured into 200 mL ice water, extracted three times with dichloromethane. The organic phases of the extract were combined, spun into silica gel, and isolated and purified by column chromatography (dichloromethane:n-hexane, v:v is 1:5) to obtain 2.4 g of white powder, MS (EI) m/z: [M]+: 713.21, with a yield of 67%.

In the embodiments of the present invention, by adding other groups on the basis of a phenazine-fused fluorene structure, organic compounds with high mobility are obtained, which enhance display performance of a display device.

An embodiment of the present invention also provides a display panel 100, which includes a light-emitting device layer 500, and the light-emitting device layer 500 includes any one of the above-mentioned organic compounds or the organic compound produced by any one of the above-mentioned preparation methods.

In the embodiments of the present invention, by adding other groups on the basis of a phenazine-fused fluorene structure, organic compounds with high mobility are obtained, which enhance display performance of a display device.

The technical scheme of the present invention will now be described in conjunction with specific embodiments.

The display panel 100 includes a substrate 200, an array substrate 300 located on the substrate 200, a light-emitting device layer 500 located on the array substrate 300, and the light-emitting device layer 500 includes any one of the above-mentioned organic compounds or the organic compounds produced by any one of the above-mentioned preparation methods. Please refer to FIG. 1 for details.

In this embodiment, the structure of the organic compound can be referred to the embodiment of any one of the above-mentioned organic compounds and the embodiment of any one of the above-mentioned methods of making organic compounds, which will not be repeated herein for brevity.

In this embodiment, the array substrate 300 includes an active layer, a first insulating layer located on the active layer, a gate layer located on the first insulating layer, and a second insulating layer located on the gate layer. Two insulating layers, a source-drain layer located on the second insulating layer and a third insulating layer located on the source-drain layer.

In this embodiment, the display panel 100 further includes an anode layer 410 on the side of the array substrate 300, a light-emitting device layer 500 on the anode layer 410, a cathode layer 420 on the light-emitting device layer 500, and, the light outcoupling layer 430 on the cathode layer 420. Please refer to FIG. 1 for details.

In this embodiment, the light-emitting device layer 500 includes a hole injection layer 510 located on the anode layer 410, a hole transport layer 520 located on the hole injection layer 510, and a hole transport layer 520 located on the hole transport layer 520. The electron blocking layer 530, the light-emitting material layer 540 located on the electron blocking layer 530, the hole blocking layer 550 located on the light-emitting material layer 540, the electron transport layer 560 located on the hole blocking layer 550, and the electron injection layer 570 on the electron transport layer 560. Please refer to FIG. 1 for details.

In this embodiment, the material in the light-emitting material layer 540 can be OLED or QLED (quantum dot light-emitting diodes), which is not limited here.

In this embodiment, the anode layer 410 includes a first ITO (Indium Tin Oxide) layer, a silver layer on the first ITO layer, a second ITO layer on the silver layer. The anode layer 410 is a totally reflective electrode, which can improve the light-emitting efficiency of the light-emitting device layer 500.

In this embodiment, the cathode layer 420 is a transparent electrode material or a semi-transparent electrode material, and may include ITO to increase the light-emitting efficiency of the light-emitting device layer 500.

In this embodiment, the light outcoupling layer 430 is used to improve the light-emitting efficiency of the light-emitting device layer 500 and enhance the display effect.

In this embodiment, the hole transport layer 520 includes the organic compound. The organic compound cooperates with the hole transport layer 520, and the hole transport efficiency can be best improved.

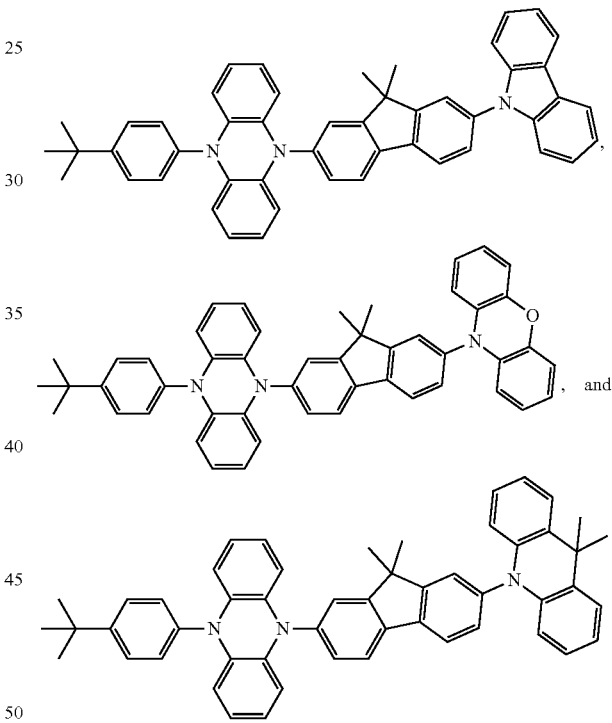

Taking as examples, the three compounds are named Compound 1, Compound 2, and Compound 3.

In this example, the HOMO electrochemical energy level of Compound 1 is −5.58 eV, and the LUMO electrochemical energy level is −2.43 eV. The HOMO electrochemical energy level of Compound 2 is −5.61 eV, and the LUMO electrochemical energy level is −2.54 eV. The HOMO electrochemical energy level of Compound 3 is −5.66 eV, and the LUMO electrochemical energy level is −2.44 eV. It can be seen that taking the three structures as examples, characterization parameters indicate that the organic compounds can be used as transporting materials.

In this embodiment, Compound 1, Compound 2 and Compound 3 are used in the hole transport layer 520.

In this embodiment, the display panel 100 including the hole transport layer 520 of the Compound 1 has the highest current efficiency of 40.1 cd/A, the red light color coordinates (CIEx, CIEy) of (0.685, 0.291), and the maximum external quantum efficiency of 36.7%.

In this embodiment, the display panel 100 including the hole transport layer 520 of the Compound 2 has the highest current efficiency of 36.8 cd/A, the red light color coordinates (CIEx, CIEy) of (0.684, 0.290), and the maximum external quantum efficiency of 34.3%.

In this embodiment, the display panel 100 including the hole transport layer 520 of the Compound 3 has the highest current efficiency of 39.8 cd/A, the red light color coordinates (CIEx, CIEy) of (0.686, 0.292), and the maximum external quantum efficiency of 35.5%.

In this embodiment, it can be seen from the above characterization data that the organic compounds of the embodiments of the present invention, taking Compound 1, Compound 2, and Compound 3 as examples, can be used in the hole transport layer 520, which has high current efficiency and higher maximum external quantum efficiency, and meanwhile the color standard of red light is more accurate. The organic compounds of the embodiments of the present invention can be used as the materials of the light-emitting device layer 500, especially as materials of the hole transport layer 520, and a better working efficiency, thus extending the service life of the display panel 100.

In the embodiments of the present invention, by adding other electron-donating groups on the basis of a phenazine-fused fluorene structure, organic compounds with high mobility are obtained, which enhance display performance of a display device.

An embodiment of the present invention also provides a display device 10, including any one of the above-mentioned display panel 100.

Figure 2:
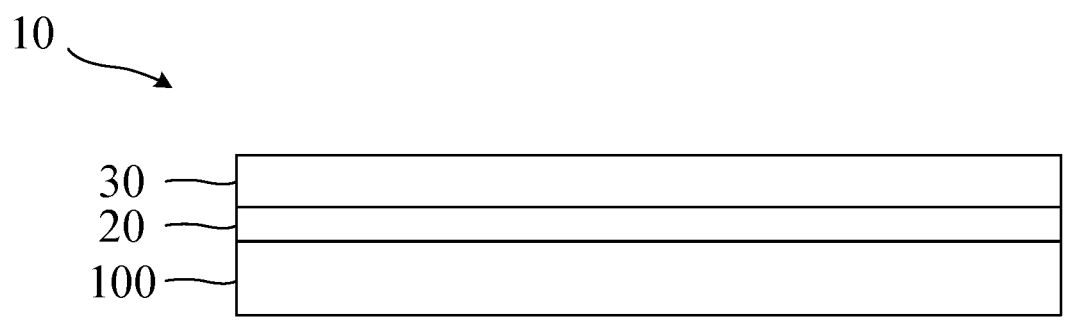
FIG. 2 is a schematic structural diagram of a display device provided by an embodiment of the present invention.

A specific structure of the display panel 100 can be referred to any one of the above-mentioned embodiments of the display panel 100, as well as FIG. 1 and FIG. 2, which will not be repeated herein for brevity.

In this embodiment, the display device 10 also includes an encapsulation layer 20 and a cover layer 30 on the display panel 100. Please refer to FIG. 2 for details.

In the embodiments of the present invention, by adding other electron-donating groups on the basis of a phenazine-fused fluorene structure, organic compounds with high mobility are obtained, which enhance display performance of a display device.

Embodiments of the present invention disclose an organic compound, a preparation method thereof, and a display panel. The organic compound is represented by the following general formula:

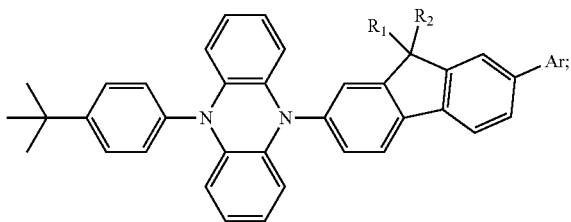

wherein Ar1 comprises any one or a combination of hydrogen, an isotope of hydrogen, an aromatic group, an arylamine group, a heteroarylamine group, and a fused ring group; and R1 and R2 are each independently any one or a combination of alkyl, alkoxy, heteroalkyl, and an aromatic group. In the embodiments of the present invention, by adding other groups on the basis of a phenazine-fused fluorene structure, organic compounds with high mobility are obtained, which enhance display performance of a display device.

It can be understood that for those of ordinary skill in the art, equivalent substitutions or changes can be made according to the technical solutions and inventive concepts of the present application, and all these changes or substitutions shall fall within the protection scope of the appended claims of the present application.

What is claimed is:

1. An organic compound, wherein the organic compound is represented by the following general formula:

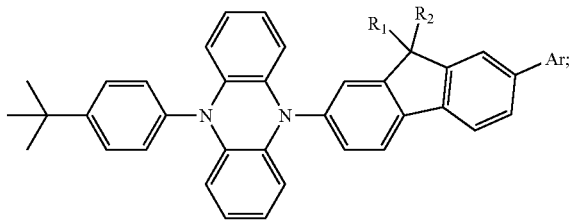

wherein Ar comprises any one hydrogen, an aromatic group, an arylamine group, a heteroarylamine group, and a fused ring group; and R1 and R2 are each independently any one or a combination of alkyl, and an aromatic group.

2. The organic compound according to claim 1, wherein Ar comprises any one protium, an aromatic group having 6 to 60 carbon atoms, an arylamine group having 6 to 60 carbon atoms, a heteroarylamine group having 6 to 60 carbon atoms, and a fused ring group having 10 to 60 carbon atoms; and R1 or R2 is any one an alkyl group having 1 to 22 carbon atoms, and an aromatic group having 6 to 60 carbon atoms.

3. The organic compound according to claim 1, wherein Ar is any one the following groups:

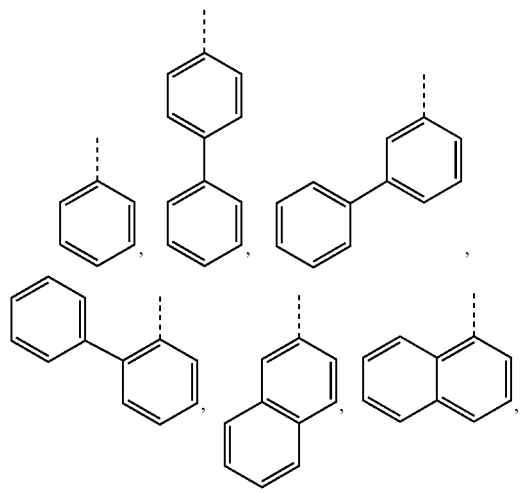

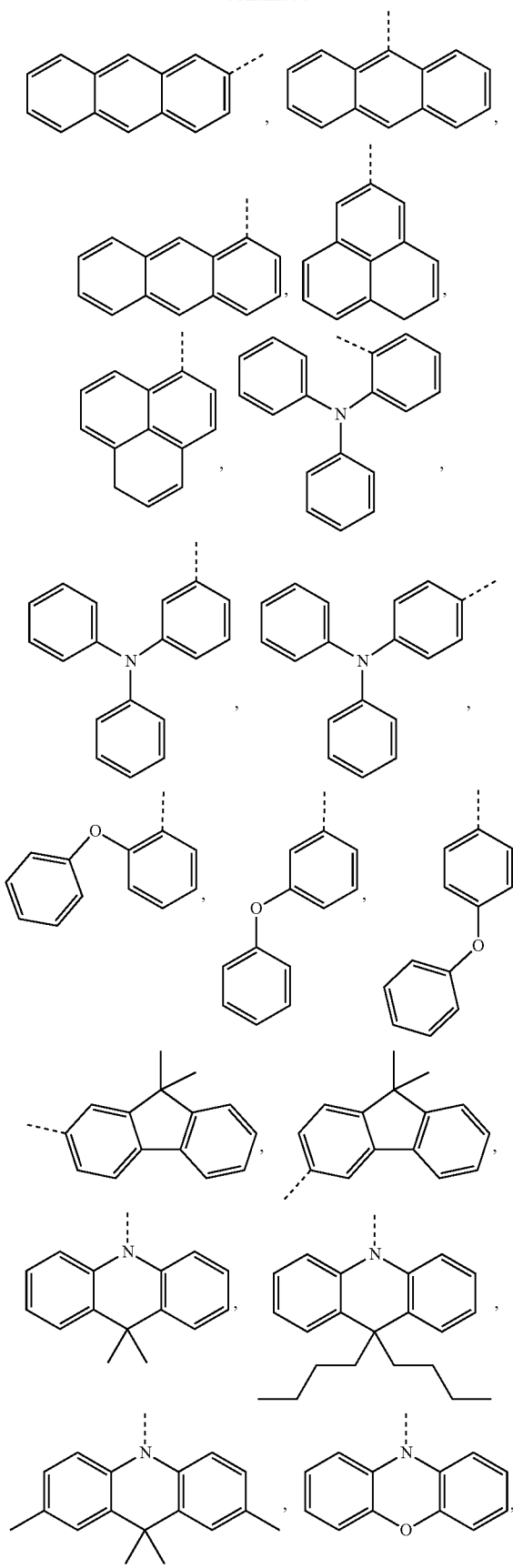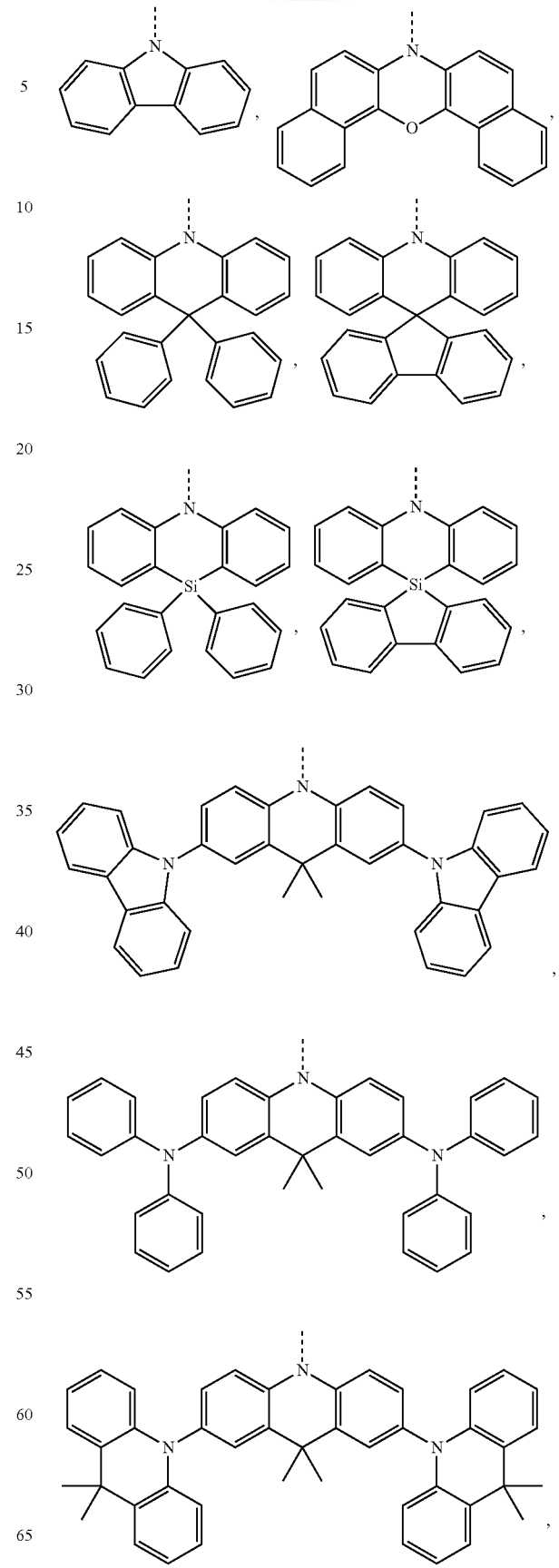

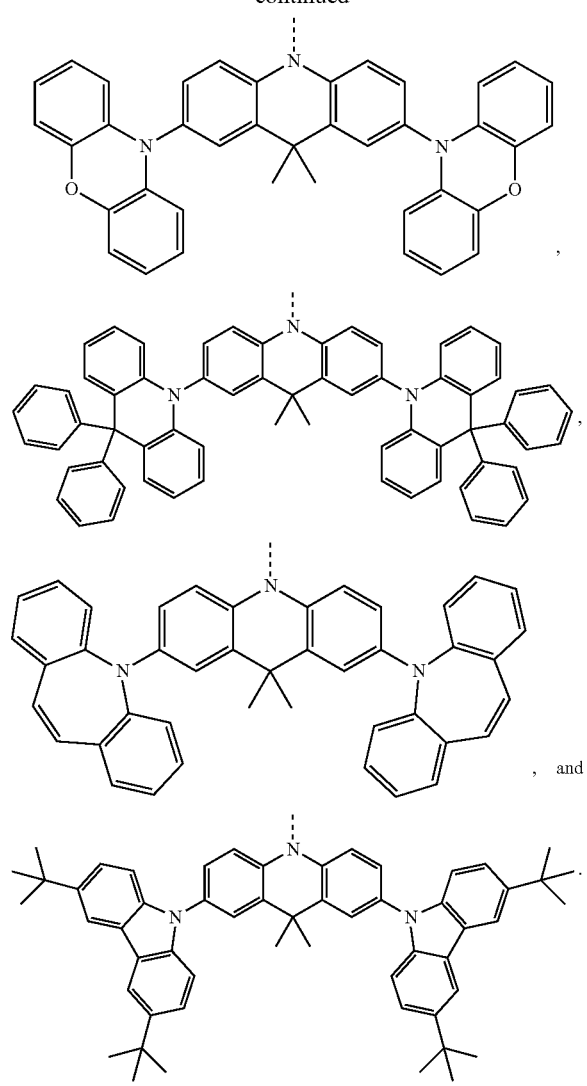
4. The organic compound according to claim 2, wherein Ar is any one the following groups:
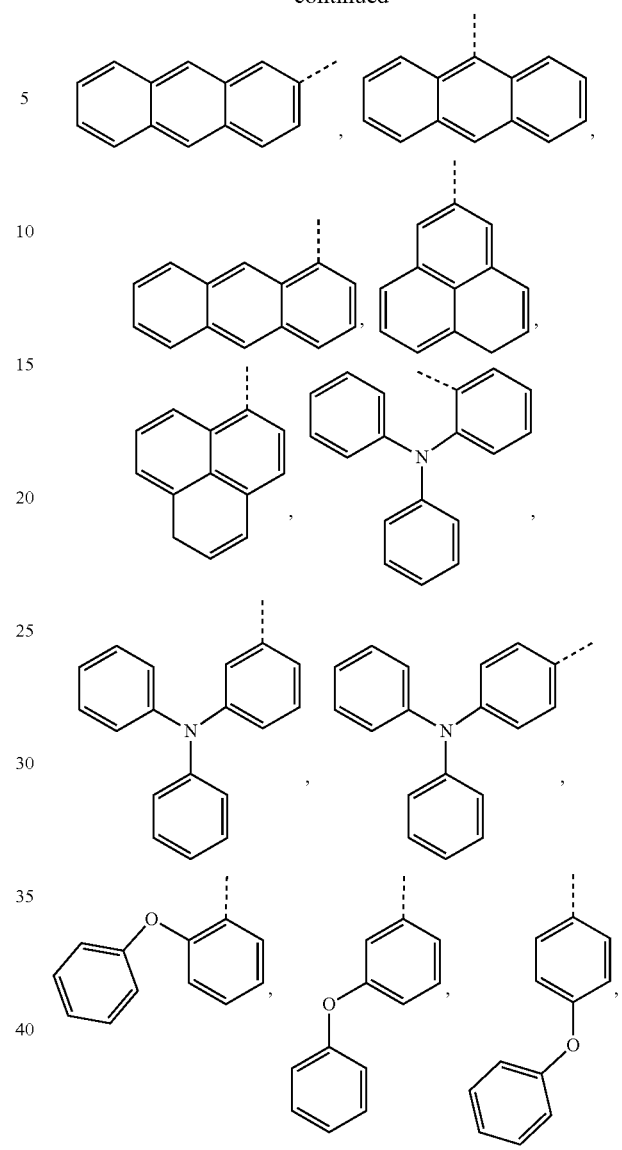

-continued

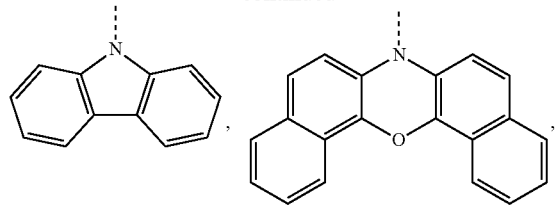

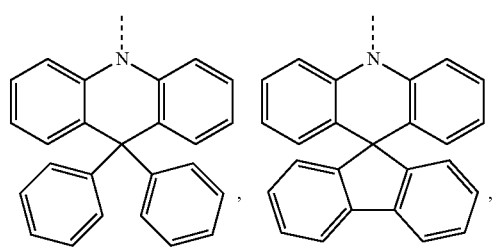

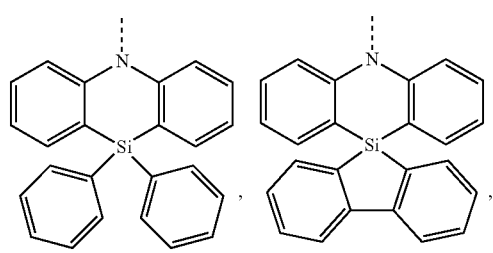

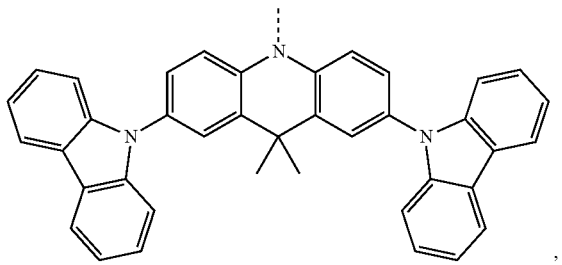

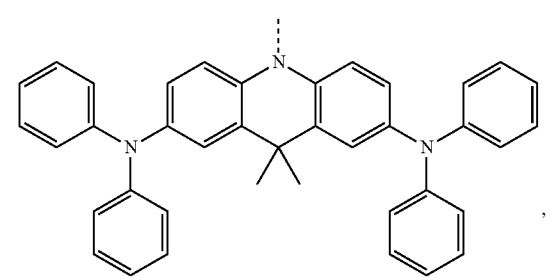

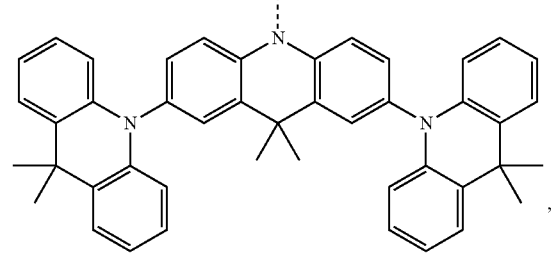

-continued

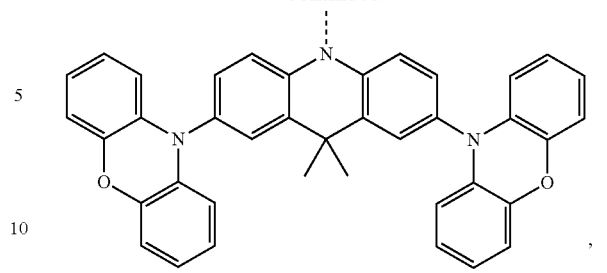

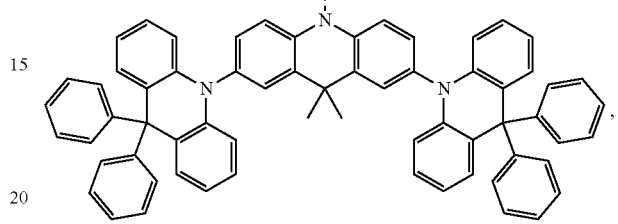

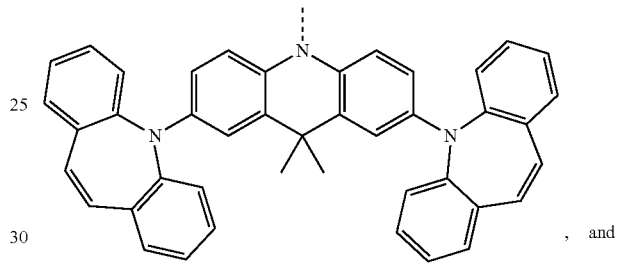

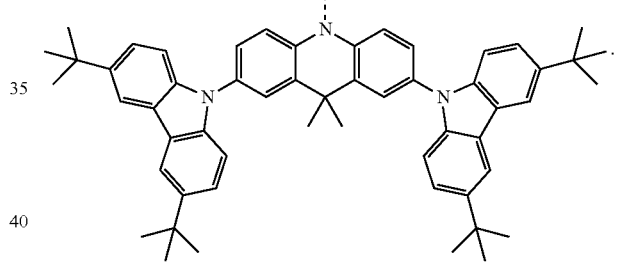

5. The organic compound according to claim 1, wherein R1 and R2 are each independently any one of methyl, ethyl, and phenyl.

6. The organic compound according to claim 1, wherein a structural formula of the organic compound is:

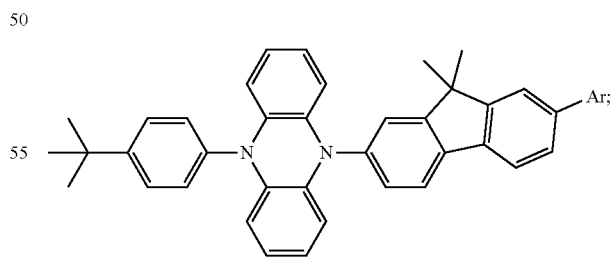

wherein Ar is an aromatic group having 6 to 60 carbon atoms or a heteroaromatic group having 6 to 60 carbon atoms.

7. The organic compound according to claim 1, wherein a structure of the organic compound comprises any one the following:

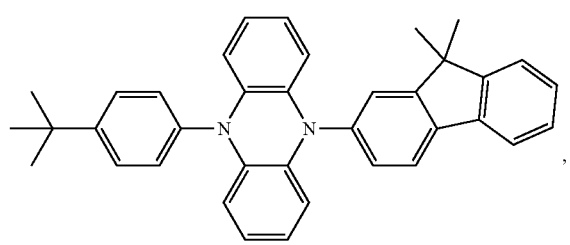,
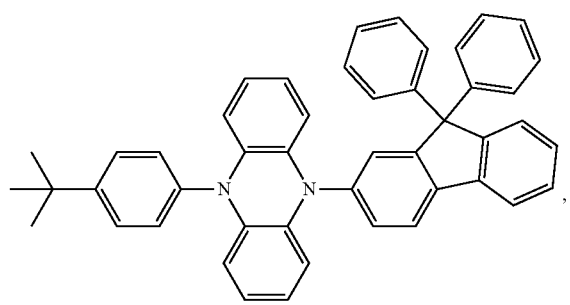,
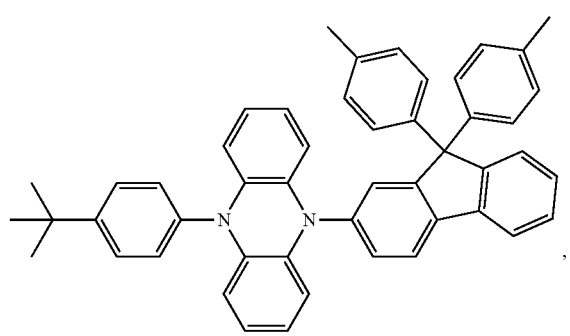,
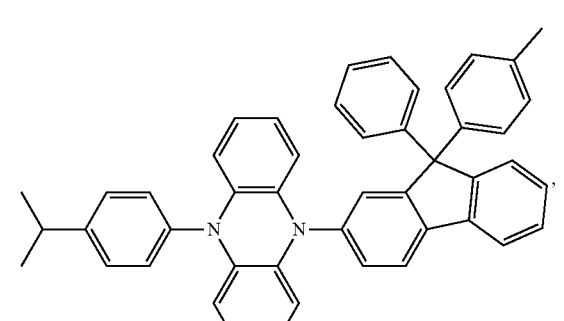,
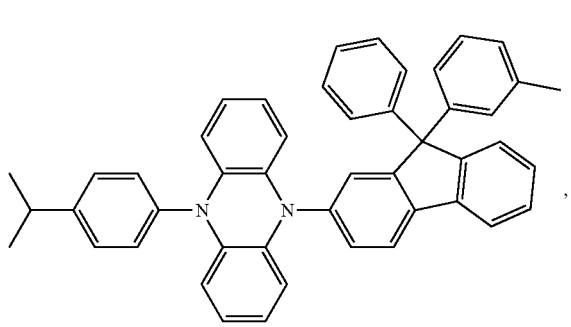,
-continued
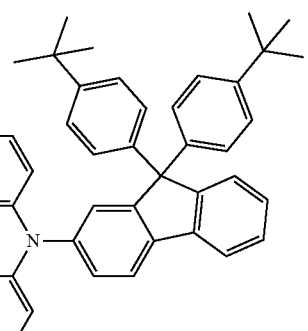,
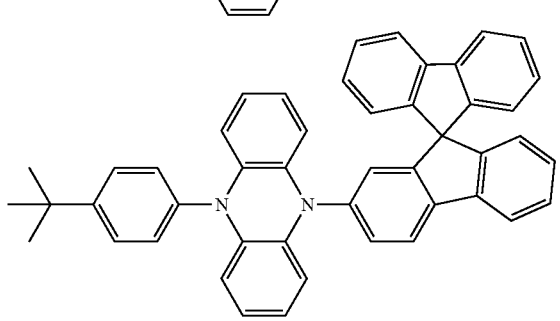,
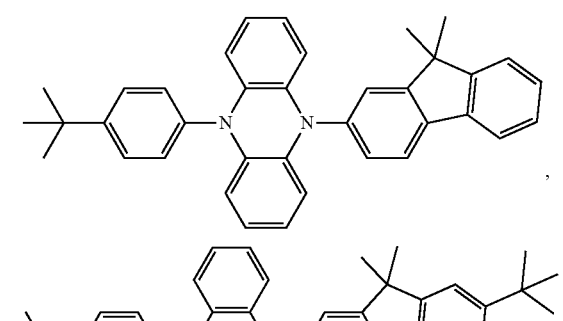,
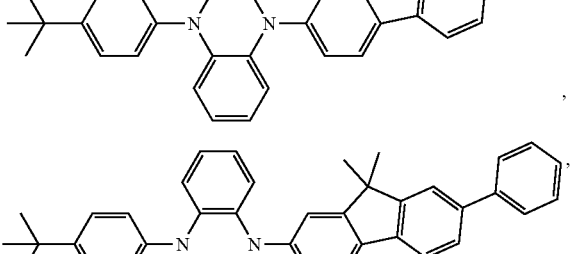,
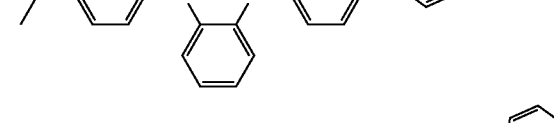,
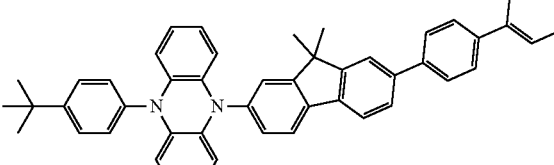,
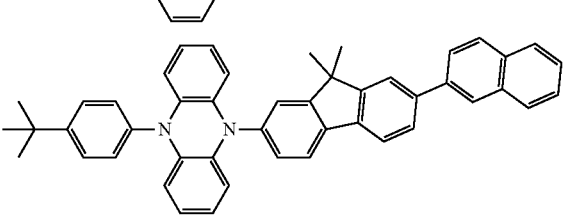,

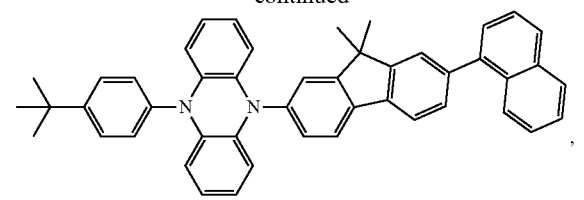,
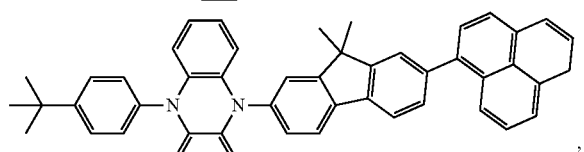,
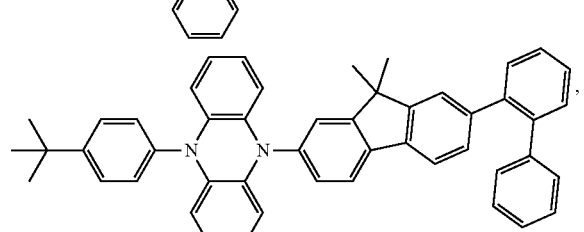,
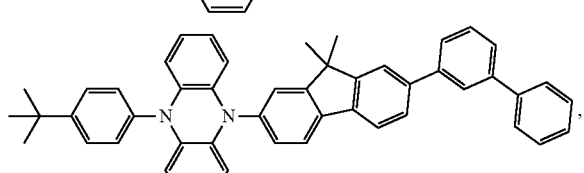,
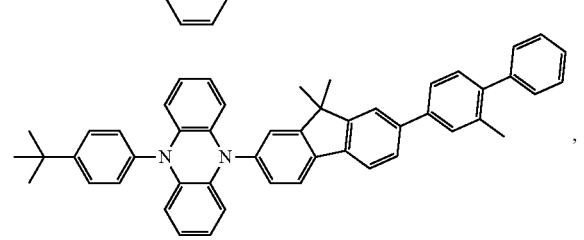,
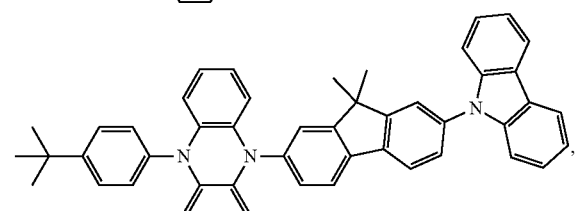,
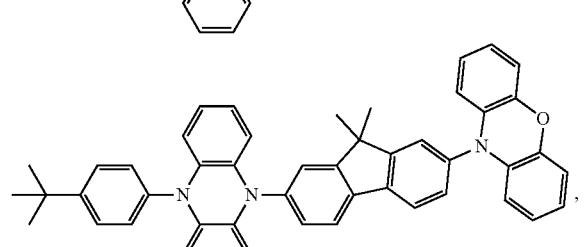,
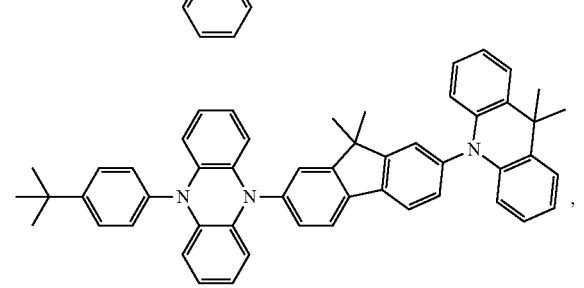,
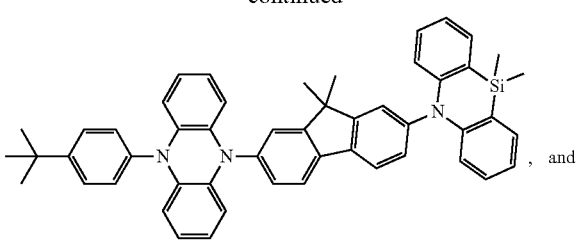, and
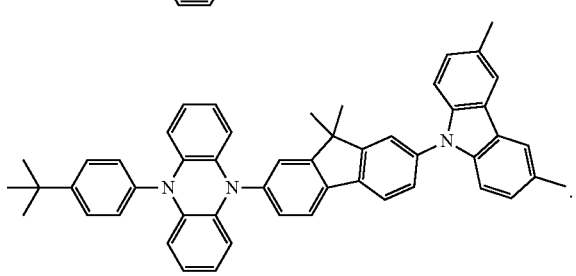.
8. A display panel, comprising a light-emitting device layer, wherein the light-emitting device layer comprises an organic compound, and the organic compound is represented by the following general formula:
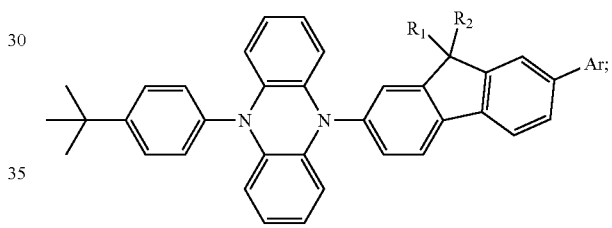
wherein Ar is any one the following groups:
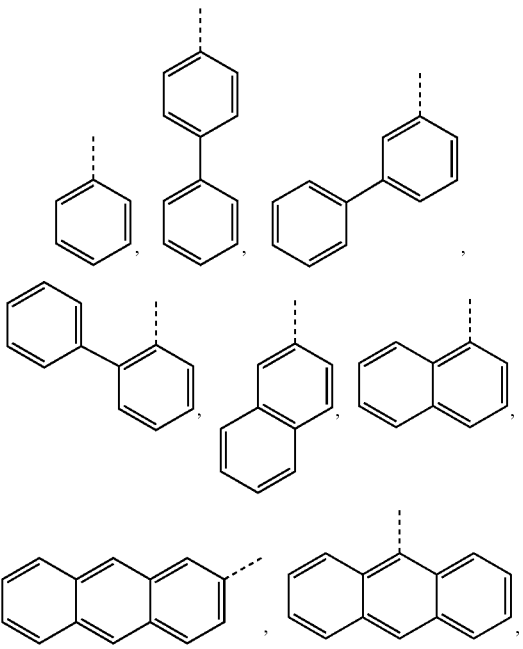

-continued
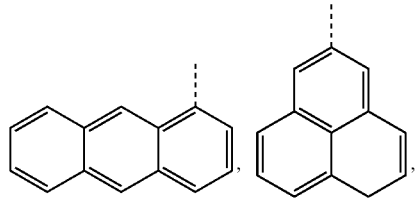
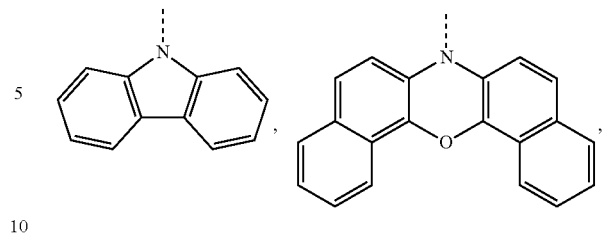
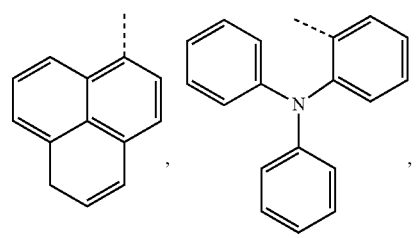
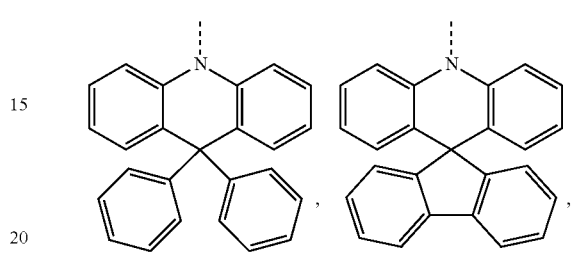
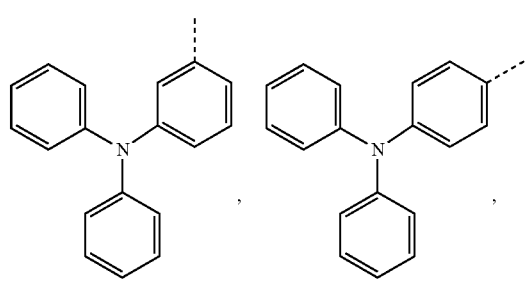
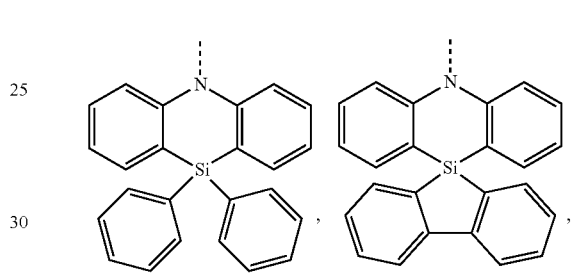
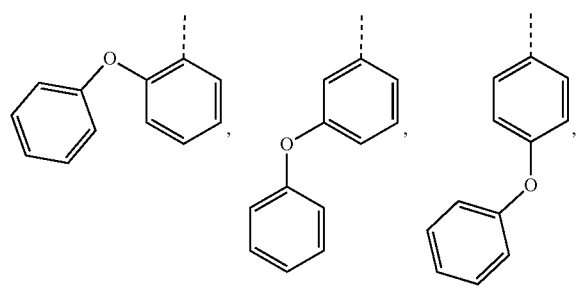
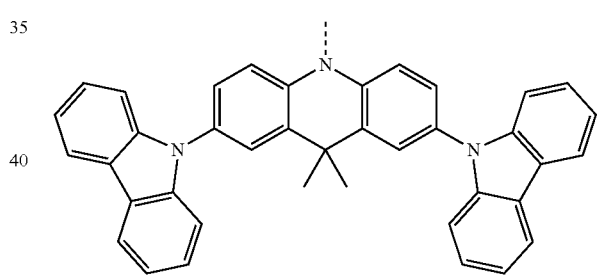
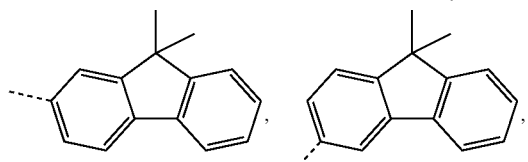
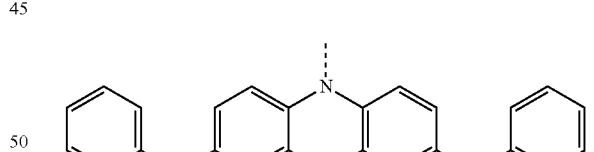
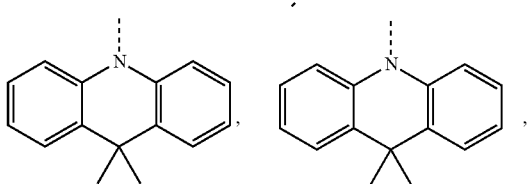
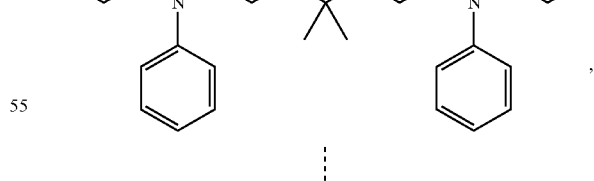
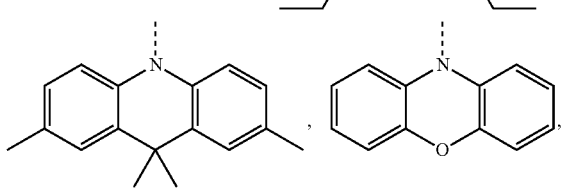
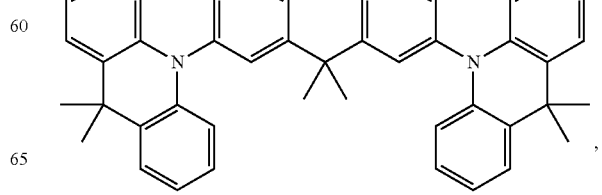

-continued

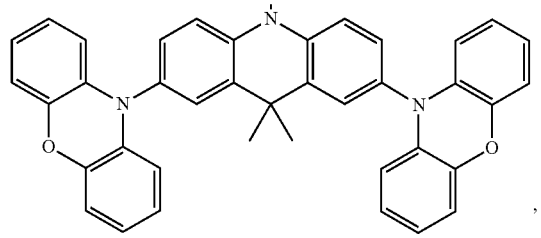

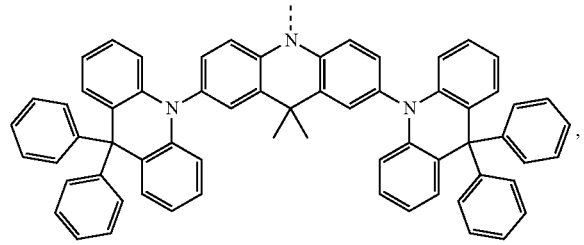

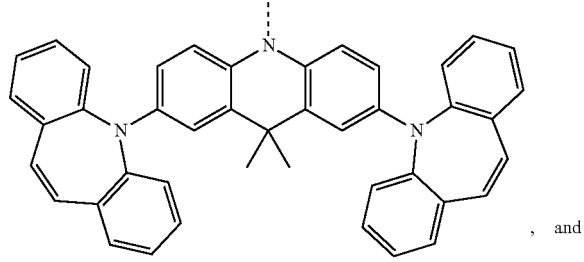

,  and

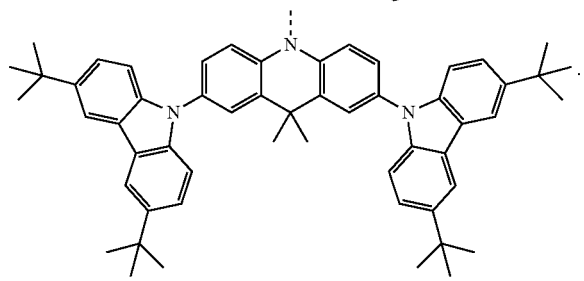

9. The display panel according to claim 8, wherein R1 and R2 are each independently any one of methyl, ethyl, and phenyl.

10. The display panel according to claim 8, wherein a structural formula of the organic compound is:

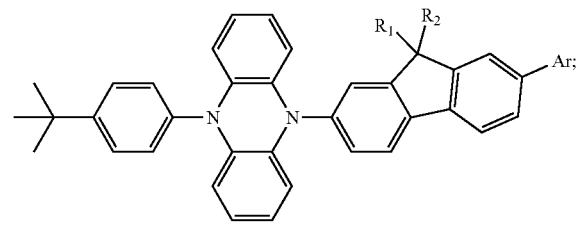

wherein Ar is an aromatic group having 6 to 60 carbon atoms or a heteroaromatic group having 6 to 60 carbon atoms.

11. The display panel according to claim 8, wherein a structure of the organic compound comprises any one the following:

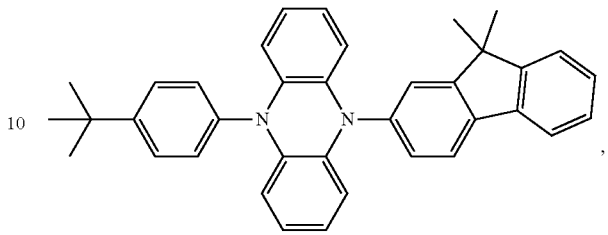

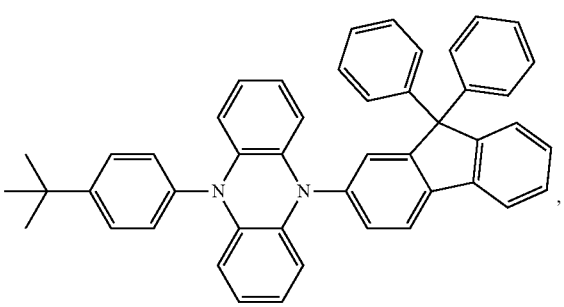

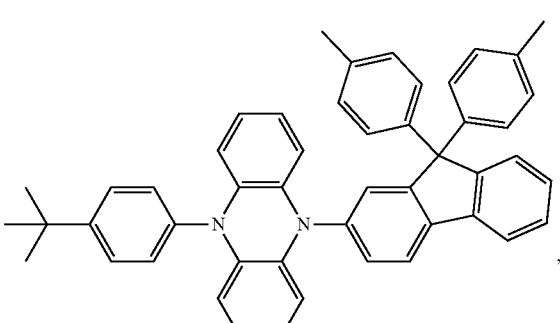

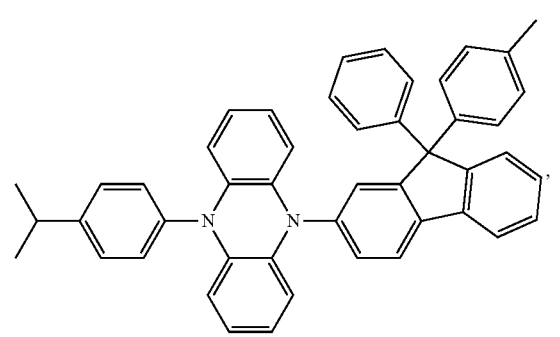

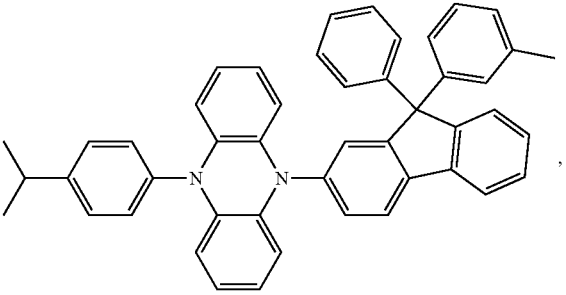

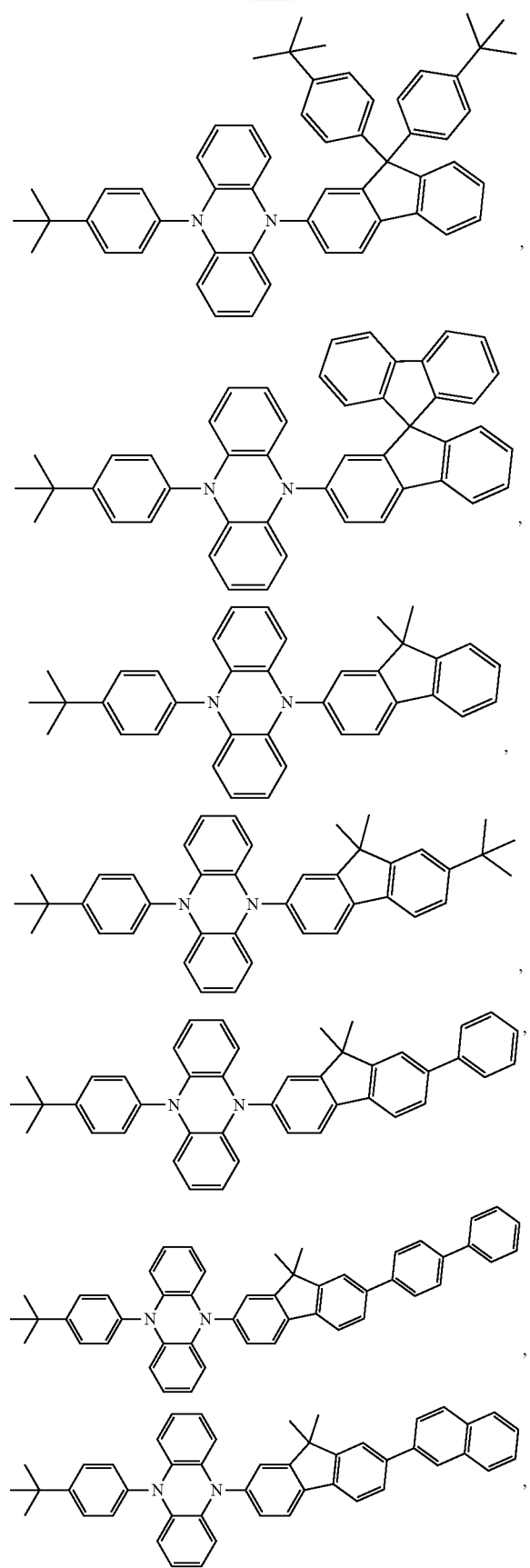
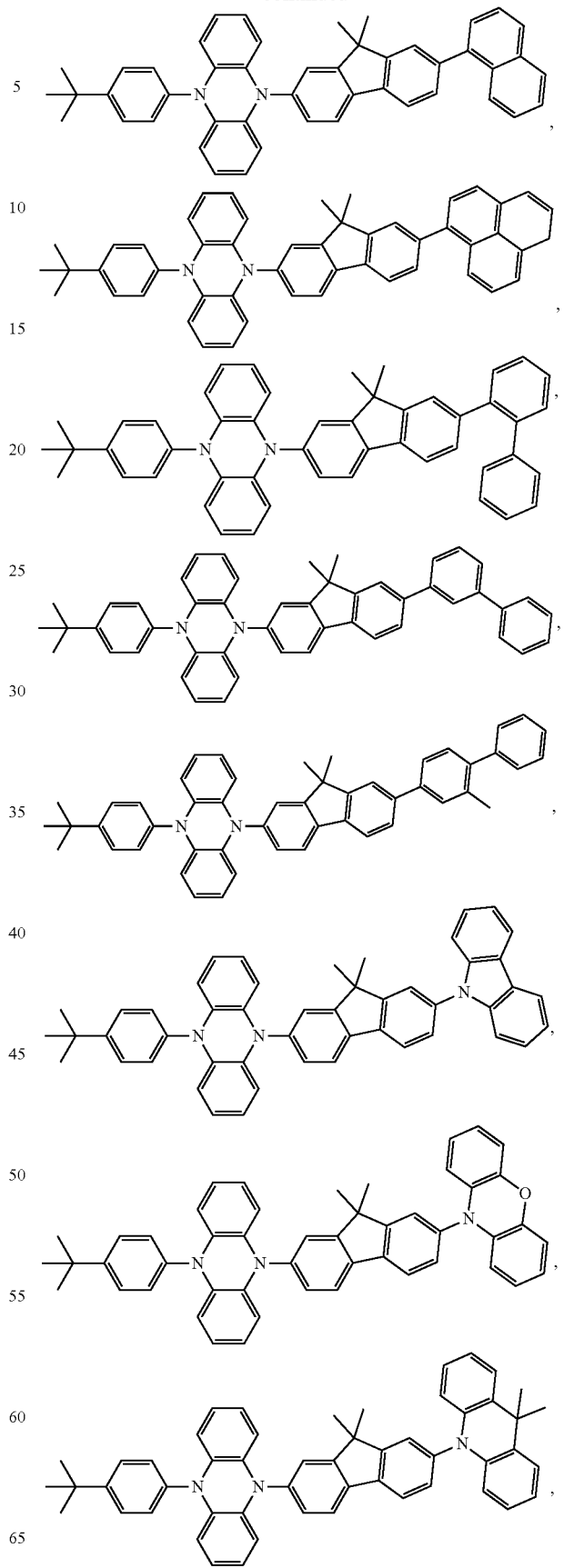

-continued
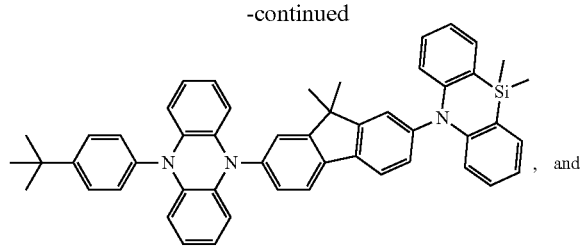, and
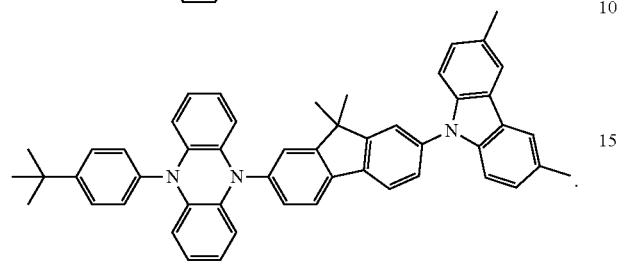.
* * * * *